US010550417B2

(12) United States Patent
Ram et al.

(10) Patent No.: US 10,550,417 B2
(45) Date of Patent: Feb. 4, 2020

(54) AUTOMATED VIABILITY TESTING SYSTEM

(71) Applicant: Wayne State University, Detroit, MI (US)

(72) Inventors: Jeffrey Ram, Huntington Woods, MI (US); Alice Hudder, Erie, PA (US)

(73) Assignee: WAYNE STATE UNIVERSITY, Detroit, MI (US)

( * ) Notice: Subject to any disclaimer, the term of this patent is extended or adjusted under 35 U.S.C. 154(b) by 211 days.

(21) Appl. No.: 14/607,976

(22) Filed: Jan. 28, 2015

(65) Prior Publication Data

US 2015/0211043 A1    Jul. 30, 2015

Related U.S. Application Data

(60) Provisional application No. 61/932,688, filed on Jan. 28, 2014.

(51) Int. Cl.
| | | |
|---|---|---|
| C12Q 1/04 | (2006.01) | |
| C12M 1/34 | (2006.01) | |
| C12M 1/36 | (2006.01) | |
| G01N 21/64 | (2006.01) | |
| G01N 33/58 | (2006.01) | |
| C12Q 1/06 | (2006.01) | |
| G01N 33/18 | (2006.01) | |

(52) U.S. Cl.
CPC ............... *C12Q 1/04* (2013.01); *C12M 41/36* (2013.01); *C12M 41/46* (2013.01); *C12M 41/48* (2013.01); *C12Q 1/06* (2013.01); *G01N 21/6486* (2013.01); *G01N 33/1806* (2013.01); *G01N 33/582* (2013.01)

(58) Field of Classification Search
CPC ........ C12Q 1/04; C12Q 1/06; G01N 21/6486; G01N 33/1806; G01N 33/582; C12M 41/36; C12M 41/46; C12M 41/48
See application file for complete search history.

(56) References Cited

U.S. PATENT DOCUMENTS

2005/0191620 A1* 9/2005 McDevitt ............. C12Q 1/6816
435/5

FOREIGN PATENT DOCUMENTS

| CN | 102140491 A | * | 8/2011 |
| WO | WO 2009/038763 A1 | | 3/2009 |

OTHER PUBLICATIONS

English language machine translation of CN102140491 (Aug. 3, 2011), 10pages.*

(Continued)

*Primary Examiner* — William H. Beisner
(74) *Attorney, Agent, or Firm* — Billion & Armitage; Michael A. Collins

(57) ABSTRACT

The invention provides an automated device for accessing the viability of a wide range of organisms based on the metabolic production of fluorescent products from non-fluorescent substrates. Also provide are methods for detecting contaminants in a fluid and measuring the viability of organisms in a fluid or liquid. Components of the invention include the incorporation of a reusable filter to concentrate the organisms, the back flush of the filter to collect the organisms for assay, and the addition of the substrate in a fluorescent detection chamber to detect the enzymatic activity produced by viable organisms to detect the presence of such organisms.

4 Claims, 19 Drawing Sheets

Schematic of Automated Fluorescence Live/Dead Assay Device

(56) References Cited

OTHER PUBLICATIONS

Adam et al., "Development of a sensitive and rapid method for the measurement of total microbial activity using fluorescein diacetate (FDA) in a range of soils", Soil Biology and Biochemistry, vol. 33 (7-8), Jun. 2001, pp. 943-951.
Balagadde et al., "Long-Term Monitoring of Bacteria Undergoing Programmed Population Control in a Microchemostat", Science, vol. 309 (5731), Jul. 2005, pp. 137-140.
Boldor et al., "Design and Implementation of a Continuous Microwave Heating System for Ballast Water Treatment", Environmental Science & Technology, vol. 42 (11), 2008, pp. 4121-4127.
Bronte et al., "Fish Community Changes in the St. Louis River Estuary, Lake Superior, 1989-1996: Is It Ruffe or Population Dynamics?", Journal of Great Lakes Research, vol. 24 (2), 1998, pp. 309-318.
Clavero et al., "Invasive species are a leading cause of animal extinctions", Trends in Ecology & Evolution, vol. 20 (3), Mar. 2005, p. 110.
Geary, "In-situ optical sensing for the detection and quantification of pathogen indicator organisms", Ph.D Dissertation, Graduate Program in Civil Engineering and Geological Sciences, Notre Dame, Indiana, Apr. 2009, 247 pages.
Haugland, "Chapter 10 Enzyme Substrates and Assays", Handbook of Fluorescent Probes and Research Products, 11th Edition, Molecular Probes, Inc., 2010, pp. 402-474.
Kelly, "Vectors and Pathways for Nonindigenous Aquatic Species in the Great Lakes", Transportation Research Board Special Report 291, Jun. 2007, 27 pages.
Mideq, "Ballast Water Control General Permit: Port Operations and Ballast Water Discharge", State of Michigan Department of Environmental Quality, Permit No. MIG140000, 2006, 23 pages.
Minnesota, "Draft ballast water discharge certification to EPA certifying compliance with section 401 Clean Water Act", USEPA, May 7, 2012, 14 pages.
Nijak, Jr. et al., "Autonomous, Wireless In-Situ Sensor (AWISS) for Rapid Warning of *Escherichia coli* Outbreaks in Recreational and Source Waters", Environmental Engineering Science, vol. 29 (1), 2012, pp. 64-69.
NSF International, "Generic Protocol for the Verification of Ballast Water Treatment Technology", Produced for the U.S. Environmental Protection Agency Environmental Technology Verification Program in Cooperation with U.S. Coast Guard and the U.S. Navy Research Laboratory, 2010, 156 pages.
Pennsylvania Sea Grant, "Round Goby", Department of Environmental Protection, Information Sheet, 2013, 2 pages3.
Pothoven et al., "Influences on Bythotrephes longimanus life-history characteristics in the Great Lakes", Journal of Great Lakes Research, vol. 38 (1), Mar. 2012, pp. 134-141.
Ram et al., "Authentication of Canned Tuna and Bonito by Sequence and Restriction Site Analysis of Polymerase Chain Reaction Products of Mitochondrial DNA", Journal of Agricultural and Food Chemistry, vol. 44, 1996, pp. 2460-2467.
Ram et al., "Identification of pets and raccoons as sources of bacterial contamination of urban storm sewers using a sequence-based bacterial source tracking method", Water Research, vol. 41 (16), Aug. 2007, pp. 3605-3614.
Ram et al., "Sequence-based source tracking of *Escherichia coli* based on genetic diversity of beta-glucuronidase", Journal of Environmental Quality, vol. 33 (3), 2004, pp. 1024-1033.
Savino et al., "An Exotic Fish in the Great Lakes", GLSC Fact Sheet, Great Lakes Science Center, Ann Arbor, 2000, 2 pages.
Schrock et al., "Mycometer®-test Rapid Fungi Detection and Bactiquant®-test Rapid Bacteria Detection Technologies", Environmental Technology Verification Report, Dec. 2011, 51 pages.
USCG, "Standards for living organisms in ships' ballast water discharged in U.S. waters", Federal Register, vol. 77 (57), Mar. 23, 2012, pp. 17254-17320.
USEPA, "Water: Habitat Protection: Invasive Species", Retrieved from http://water.epa.gov/type/oceb/habitat/invasive_species_index.cfm, accessed Oct. 10, 2015, 1 page.
Vanderploeg et al., "Dreissena and the disappearance of the spring phytoplankton bloom in Lake Michigan", Journal of Great Lakes Research, vol. 36, 2010, pp. 50-59.
Welschmeyer et al., "Dreissena and the disappearance of the spring phytoplankton bloom in Lake Michigan", Retrieved from http://www.psmfc.org/ballast/wordpress/wp-content/uploads/2010/01/WelschmeyerPBWG-2010-Recovered.pdf, 2010, 41 pages.
Wright et al., "Shipboard testing of the efficacy of SeaKleen® as a ballast water treatment to eliminate non-indigenous species aboard a working tanker in Pacific waters", Environmental Technology, vol. 30 (9), 2009, pp. 893-910.

\* cited by examiner

A.

B.

| | Quanti Tray Data | |
|---|---|---|
| | MPN of Coliforms | MPN of E.Coli Coliforms |
| Rock Harbor Direct (RHD) | 128.1 | 2.0 |
| Ballast Water Intake (BWI) | 6.3 | 1.0 |
| Ballast Water Discharge (BWD) | <1 | <1 |
| Portage Canal Direct (PCD) | 39.9 | 2.0 |
| Sterile Water Control (SWC) | <1 | <1 |

AUTOMATED VIABILITY TESTING SYSTEM

BACKGROUND OF THE INVENTION

Keeping aquatic environments free of invasive species is important for healthy, sustainable aquatic ecosystems. Methods to reduce the transport of non-native or invasive species are critical to not only aquatic systems, but to overall environmental and ecosystem health. As awareness of the damage caused by invasive species increases, international, national, and state regulations are changing to require the use of treatment systems to greatly limit, reduce or eliminate opportunities for unwanted live organisms to enter aquatic environments. Accordingly, there is a need for methods to measure and protect our aquatic environments and ecosystems from non-beneficial, non-indigenous or pest species.

SUMMARY

The invention provides an automated biological live/dead analysis system that provides real-time verification of ballast water treatment systems. The ballast water treatment systems of the invention prevent the discharge of ballast waters, or other waters, containing live organisms into aquatic systems. The invention further provides that the automated system is able to be located on a ship for ease of use and access to ballast water. The invention also provides an automated system that prevents the discharge of ballast waters containing live organisms into an aquatic environment. The invention also provides methods systems and devices that can be operated on site or remotely from any location worldwide. As a non-limiting example, the operation of the methods, systems and devices of the invention can be done via internet connection, enabling the operation of the methods, systems and devices of the invention, as well as receiving data from the performed testing, from any location desired.

Further provided is a method of analyzing water to ensure compliance with applicable laws, statutes, rules, regulations, standards, guidelines and ordinances. Also provided is a method of analyzing environmental samples. The invention further provides methods of reducing future invasions of undesirable organisms into aquatic systems. Any of the devices provided herein can be used in methods of reducing invasions of pest organisms in aquatic systems. The invention also provides methods to slow the spread of non-native invasive organisms in aquatic environments by enabling prompt enforcement of current and planned water regulations, including ballast water regulations. Any of the devices provided herein can be used in methods to slow the spread of non-native invasive organisms in aquatic environments.

The devices and systems of the invention can be engineered into the existing ballast system of a ship or other craft, so that no manual sampling is required. The methods, devices and systems of the invention use highly sensitive detection system to detect any living organisms in the sample tested. The highly sensitive detection system of the invention is a fluorescence based system, but could be modified to other methods of detection to identify specific species, family or phyla of organisms.

In one embodiment, the invention provides an automated biological live/dead analysis test system for determining the presence or absence of live organisms in water. The water contemplated to be tested in the systems can be from any source, including the ballast water of a ship, open water sources, water run-off, waste water or a municipal drinking water system.

The invention additionally provides a method for detecting contaminants or live organisms in a fluid, comprising passing a known volume of a fluid through a reusable filter from an influent side to an effluent side, wherein the filter is housed in a filter assembly or filter assembly, and whereby the contaminants or organisms are retained on the influent side of the filter in the filter assembly, discarding the fluid that passed through the filter, passing a known volume of a wash solution through the filter from an effluent side, wherein the contaminants or organisms retained on the influent side of the filter are forced from the filter and into the wash solution, passing the wash solution into a vessel, passing an amount of a substrate into the vessel, optionally placing the vessel in a detection chamber, and performing a quantitative or qualitative detection of the presence of contaminants in the fluid sample.

The invention further provides a method for measuring the viability of organisms in a fluid, comprising passing a known volume of fluid through a filter, wherein said filter is reusable, said fluid is passed through the filter in one direction, and said organisms are retained on the filter, discarding the fluid following the pass through the filter, passing a wash solution containing a substrate through the filter from the opposite direction to create a backflush sample, wherein the organisms retained on the influent side of the filter are forced from the filter and into the wash solution, flowing the backflush sample into a vessel, flowing an amount of a substrate into the vessel, placing the vessel in a detection chamber, and using a detection chamber, detecting the number of viable organisms, or alternatively, specific organisms, in the fluid sample.

Provided herein are methods for detecting contaminants in a fluid, comprising passing a known volume of a fluid through a reusable filter from an influent side to an effluent side, wherein the filter is housed in a filter assembly, whereby the contaminants are retained on the influent side of the filter in the filter assembly, discarding the fluid that passed through the filter, passing a known volume of a wash solution through the filter from an effluent side, wherein the contaminants retained on the influent side of the filter are forced from the filter and into the wash solution, passing the wash solution into a vessel, passing an amount of a substrate into the vessel; and using a detection apparatus, performing a quantitative or qualitative detection of the presence of contaminants in the fluid sample. Optionally, in certain embodiments of the methods provided herein, before passing a known volume of fluid through a reusable filter, the fluid is passed through a prefilter that does not retain the contaminants, but retains particles greater in size than the contaminants. In other embodiments, the methods of the invention are automated and can be monitored remotely. In still other embodiments of the methods of the invention, the substrate flows into the vessel by an automatic rotary valve driven injector or a pump.

The filters or filter assemblies used in the methods of the invention have a pore size of at least about 0.1 µm, and a pore size of at most about 50 µm.

The methods of the invention further comprise the use of a detection apparatus for detecting the number of viable organisms in the fluid sample. In certain embodiments, the detection is carried out using spectroscopy or a fluorimeter. In some embodiments of the methods of the invention, the substrate is a non-fluorescent substrate, such as, but not limited to, fluorescein diacetate.

The contaminants detected using the methods of the invention include, but are not limited to one or more of bacteria, fungi, algae, protozoans, spores from bacteria, spores from fungi; spores from pollen, or fragments thereof. In the methods of the invention, the fluid to be tested may comprise water, or any fluid, as well as environmental water, ballast water, recreational water, drinking water, hot water, industrial water, or process water.

Further provided is an automated device for detecting contaminants in a fluid, where the device comprises three (3) or more chambers fluidly connected to at least one filter assembly, one or more pumps, a vessel, and a detection apparatus.

Additionally provided is an automated device for detecting microorganisms in a fluid, where the device comprises three (3) or more chambers fluidly connected to at least one filter assembly, one or more pumps, one or more valves, a vessel, and a detection apparatus.

In certain embodiments, the chambers of the devices of the invention are fluidly connected to one or more valves, and in other embodiments, the valves control the flow of fluids through the chambers.

In further embodiments, the devices of the invention comprise a first chamber that is adapted to receive a fluid to be tested, a second chamber that is adapted to receive backwash fluid, a third chamber that is adapted to receive discarded fluid, a fourth chamber that is adapted to contain a substrate, and the vessel, which is adapted to receive filtered fluid for testing.

In still other embodiments, the device also comprises a pump or an automatic rotary valve-driven injector, which is adapted to force the substrate into the vessel.

Additionally, in an embodiment of the device, the detection apparatus is a spectrometer.

In other embodiments, the devices of the invention are automated and can be monitored remotely.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

DETAILED DESCRIPTION

Definitions

Figure 1:
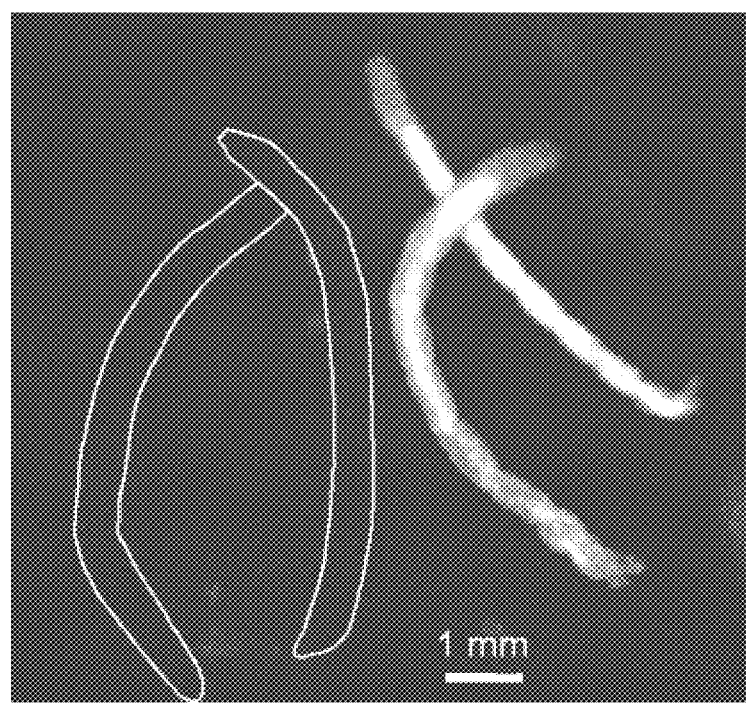
FIG. 1 illustrates *Chironomus riparus* with FDA staining. Outlined: heat-killed, not fluorescent. Bright/non-outlined: live, fluorescent.

As used herein, the recited terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* 14th Edition, by R. J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with the recitation of claim elements or use of a "negative" limitation.

The term "and/or" means any one of the items, any combination of the items, or all of the items with which this term is associated. The phrase "one or more" is readily understood by one of skill in the art, particularly when read in context of its usage. For example, one or more substituents on a phenyl ring refer to one to five, or one to four, for example if the phenyl ring is disubstituted.

The term "about" can refer to a variation of ±5%, ±10%, ±20%, or ±25% of the value specified. For example, "about 50" percent can in some embodiments carry a variation from 45 to 55 percent. For integer ranges, the term "about" can include one or two integers greater than and/or less than a recited integer at each end of the range. Unless indicated otherwise herein, the term "about" is intended to include values, e.g., weight percents, proximate to the recited range that are equivalent in terms of the functionality of the individual ingredient, the composition, or the embodiment.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. A recited range (e.g., weight percents or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, as used in an explicit negative limitation.

As used herein, the terms "device" and "apparatus" may be used interchangeably.

The term "contacting" refers to the act of touching, making contact, or of bringing to immediate or close proximity, including at the cellular or molecular level, for example, to bring about a physiological reaction, a chemical reaction, or a physical change, e.g., in a solution, in a reaction mixture, in vitro, or in vivo.

An "effective amount" refers to an amount effective to treat a disease, disorder, and/or condition, or to bring about a recited effect. For example, an amount effective can be an amount effective to reduce the progression or severity of the condition or symptoms being treated. Determination of an effective amount is well within the capacity of persons skilled in the art, especially in light of the detailed disclosure provided herein. The term "effective amount" is intended to include an amount of a compound described herein, or an amount of a combination of compounds described herein. Thus, "effective amount" generally means an amount that provides the desired effect.

A "fluid" refers to a substance that has no fixed shape and readily yields to external pressure. A fluid is a composition that can flow in response to gravity or another external force. A fluid is typically a gas or a liquid. The fluids described herein are typically aqueous fluids, such as aqueous solutions, aqueous suspensions, aqueous dispersions, water, mixtures of solids and water, or combinations of any of the preceding compositions. Specific examples of fluids include environmental samples, environmental water, ballast water, drinking water, hot water, industrial water, industrial discharge, industrial runoff, agricultural runoff, recreational water, recreational aquatic samples, recreational environmental samples, swimming pool water, process water, water treatment containers or facilities, holding tanks, septic tanks, wells, beaches, lakes, rivers, ponds, pools, inland bodies of water, basins, creeks, inland seas, lagoons, lakelets, lochs, millponds, mouth, reservoirs, sluices, springs, tarns, any sort of fluid discharge that can include microorganisms, and the like. A fluid can also be air, such as, for example, ventilation air that could contain spores or microorganisms. The fluid used to analyze a sample can be the same or different than the fluid that is originally filtered.

As used herein, the term "contaminants" relates to undesired constituents of biological origin in a sample. Non-limiting examples of contaminants are microorganisms, both pathogenic and non-pathogenic, and fragments of such microorganisms. Non-pathogenic contaminants may be undesired because they are detrimental to the quality of a product or the health of an ecosystem when they appear therein (for example, contaminating microorganisms in a controlled fermentation, contaminating microorganisms in food products that influence taste and appearance).

A "viable" or "live" microorganism is in the present context a microorganism or spore that under the right set of circumstances is or can become metabolically active. The term thus includes within its scope microorganisms that can readily be cultured, but also those that will only multiply under circumstances that are difficult to reproduce in culture.

The term "filter" is in the present context a device that excludes passage of particles larger than a certain size. A filter, as used in the invention, can be created to have a pore size of about 50 µm to about 0.01 µm. However, the term can also embrace a device that excludes passage of material that has a significant binding specificity towards a binding partner (such as a receptor, an antibody or fragments thereof). Therefore, the term also embraces devices not normally regarded as "filters", e.g. membranes in centrifuges and ultracentrifuges, membranes impregnated with specific binding partners such as antibodies or other specifically binding substances, as well as fine meshes and similar materials. Specialized "filters" contemplated by the present invention thus also include columns for affinity chromatography or membranes that impact affinity chromatography qualities—the important features of a "filter" according to the present invention are that it can retain contaminants of interest and allow a subsequent in situ reaction between a substrate and an enzyme specific for the contaminants so that a subsequent measurement of a detectable moiety derived from the substrate can be readily performed. Useful filters can often have pore sizes of about 0.01 µm to about 10 µm. Prefilters having larger sized pores can be useful, such as prefilters having pore sizes of about 10 µm to about 50 µm, or larger. The size of the filter can depend on what organism is being tested for, particulates in the water, flow, volume and desired sensitivity. Membranes can be made of any suitable and effective material such as polyvinylidene fluoride, polyethersulfone, mixed cellulose esters, track-etched polycarbonate, polytetrafluoroethylene, or other similar materials.

The term "prefilter" as used herein refers to a filter used to remove particles greater in size than the contaminants. A prefilter, as used in the invention, can be used to filter particles greater in size than the contaminants from the sample, prior to the sample being passed through the filter that can retain the contaminants.

The term "effluent" refers to the outflow of the sample, after the sample as passed through the filter. The term "influent" refers to the sample as it flows into the filter.

The term "substrate" means a chemical agent that undergoes an enzyme-catalyzed conversion in its chemical structure.

The term "detectable moiety" denotes a chemical entity which is the result of an enzyme-catalyzed conversion of a substrate, where the chemical entity comprises a physical or chemical characteristic which can be detected and which is not detectable in the substrate. Examples are fluorescent moieties, luminescent moieties, and moieties that bind with high specificity to a binding partner.

The phrase "detection apparatus," "detection machine" or "measuring system", as used herein, refers to a device or machine capable of measuring the amount of or identifying the presence of some substance, organism, entity, compound and the like. In certain embodiments of the invention, a spectrometer is a detection apparatus.

The term "vessel" as used herein refers to a container, including but not limited to a tube, a cup or a cuvette, capable of holding or containing a fluid.

The term "signal" is intended to denote the measurable characteristic of a detectable moiety as it is registered in an appropriate measuring system or detection system.

As used herein, the term "microorganism" refers to any microscopic or submicroscopic organism, including, but not limited to bacteria, fungi, archaea, protists, protozoa, spores, viruses, and prions.

As used herein, the phrase "ballast water" refers to water that is carried in the tanks of ships. To maintain stability during transit along coasts and on open water, ships, boats and other vessels fill their tanks ("ballast tanks") with water.

Large ships frequently carry millions of gallons of ballast water. This water is taken from coastal port areas and transported with the ship to the next port of call where the water may be discharged or exchanged. The aquatic environment of coastal port areas contains a diverse population of organisms that live in the water and on bottom sediments. When the ballast tank of a ship is loaded with water, the water contains many of the organisms living in that port. The ballast water of shipping vessels has been a primary method of alien or invasive species introduction throughout the world. It is estimated that as many as 3,000 alien species per day are transported in ships around the world. Not all transported species survive the journey and their new environment. However, some species do survive, and are able to flourish in their new environment. Invasive species can cause very serious disruptions in a natural ecosystem.

As used herein, the phrase "invasive species" is used to describe a species that is non-native to a particular ecosystem and whose introduction into the ecosystem causes or is likely to cause economic or environmental harm or harm to the health of the native species in the ecosystem. Non-native or invasive species include, but are not limited to, plants, insects, fish, mollusks, crustaceans, pathogens, bacteria, fungi, mammals, birds, reptiles, and amphibians. In the United States alone, invasive species have infested hundreds of millions of acres of land and water, resulting in massive disruptions in ecosystem function and health, reducing biodiversity, and degrading ecosystem health in forests, prairies, mountains, plains, wetlands, rivers, inland waters, and oceans. The native species detrimentally impacted by invasive organisms include, but are not limited to, vegetation and plants, agricultural land, microorganisms of the soil and water, forests and rangelands, as well as wildlife, rodent populations, livestock, fish and other aquatic species, animals, including mammals and humans, reptiles, and fowl.

Invasive species are considered to be in the top tier of the biggest threats to the health of aquatic environments and systems. By way of a non-limiting example, invasive species have long been considered a threat to the health of the Great Lakes ecosystems. In aquatic environments, non-native organisms compete with or kill organisms, reduce biodiversity, and cause significant economic harm. Recent examples of invasive species include zebra mussels and quagga mussels (significant changes in phytoplankton density and composition (Vanderploeg et al., 2010)), *Bythotrephes* (a less palatable zooplankton food than native water fleas (Pothoven et al., 2012)), freshwater gobies ("junk" competitor for more desirable recreational fish (Savino and Kostich, 2000)), and the ruffe (displaced 90% of natural fish populations in rivers they have infested (Bronte et al., 1998)). Presently, the costs in the United States alone of invasive species are estimated to be more than $5 billion annually. Worldwide, invasive species are thought to be the second most common cause for extinction and loss of diversity of aquatic species (Clavero and Garcia-Berthou, 2005; USEPA, 2012).

As used herein, "Concentrated Animal Feeding Operations," CAFO, and AFO may be used interchangeable and refer to an animal agricultural facility that has a potential pollution profile. CAFOs are agricultural operations where animals are kept and raised in confined situations. CAFOs congregate animals, feed, manure and urine, dead animals, and production operations on a small land area. Feed is brought to the animals rather than the animals grazing or otherwise seeking feed in pastures, fields, or on rangeland. The EPA defines a CAFO as an animal feeding operation (AFO) that (a) confines animals for more than 45 days during a growing season, (b) in an area that does not produce vegetation, and (c) meets certain size thresholds. The methods of the invention can be used to monitor water going into and out of a CAFO operation. The methods of the invention can also be used to monitor or measure potential pathogens in water going into a CAFO operation, which helps to ensure the health of the animals and humans working in proximity to the water. Additionally, the methods of the invention can be used to monitor or measure potential pathogens in water or discharges (liquid discharges or diluted solid discharges) from a CAFO facility. Further, the methods of the invention can be used to monitor or measure potential pathogens in waste produced by a CAFO operation, as well as in local or regional water supplies around a CAFO operation, or in proximity to a CAFO operation.

The ramifications of contamination to and from a CAFO facility are well documented. The concentration of the wastes from the animals in CAFOs increases the potential to impact air, water, and land quality. Failures to properly manage manure and wastewater at CAFOs can negatively impact the environment and public health. As a non-limiting example, manure and wastewater have the potential to contribute pollutants, such as nitrogen and phosphorus, organic matter, sediments, pathogens, heavy metals, hormones and ammonia, to the environment.

As another non-limiting example, the environmental impacts resulting from mismanagement of wastes include excess nutrients in water (such as nitrogen and phosphorus), which can contribute to low levels of dissolved oxygen (fish kills), and decomposing organic matter that can contribute to toxic algal blooms. Contamination from runoff or lagoon leakage can degrade water resources, and can contribute to illness by exposing humans and other animals to wastes and pathogens in their drinking water. Dust and odors can contribute to respiratory problems in humans living and/or working near a CAFO.

Reducing non-native species in the Great Lakes of the United States is essential to Great Lakes ecosystem health. Since 1959, about 30-55% of non-native species that entered the Great Lakes are estimated to have done so by being transported in ballast water from foreign ports (Kelly, 2007). Ballast water is taken onto or discharged from a ship as it loads or unloads its cargo, to accommodate changes in its weight. In the early 1990's, the U.S. Coast Guard began requiring ships to exchange their ballast water, or seal their ballast tanks for the duration of their stay, in order to lessen the entrance of invasive species into the Great Lakes. The Coast Guard later used their success in the Great Lakes to develop a ballast management program for the entire United States.

Therefore, ballast water has been the focus of significant attention in order to protect, restore and maintain Great Lakes ecosystem health. Increasingly stringent international, national, and state regulations may require ballast water treatment (herein referred to as "BWT") systems to be employed to thwart the entrance of invasive species into ecosystems like the Great Lakes, and other ecosystems. Additionally, international, national, and state regulations may require the functions of BWT systems to be verified in order to effectively eliminate the discharge of live organisms into the aquatic environments and ecosystems, including, but not limited to, the Great Lakes (for example, (Minnesota, 2012; see also USCG, 2012, p 17305)).

At every level of government, laws, statutes, rules, regulations and ordinances have been enacted and enforced to address a wide range of efforts to reduce, inhibit, or eliminate the entrance of non-native species into aquatic environments and ecosystems. It is expected that governments will continue and expand efforts to reduce, inhibit, or eliminate the entrance of non-native species into aquatic environments and ecosystems.

As a non-limiting example, regulations by the International Maritime Organization (IMO) and various US and Canadian jurisdictions (USGS, Great Lakes, and others) require verification that ballast water from ships has been tested for live organisms and that ballast water treatment systems (BSTs) virtually eliminate all live organisms from ballast water discharges. As another non-limiting example, proposed rules of the State of Minnesota, U.S.A., which were published for public comment on May 7, 2012, require both ballast water exchange and treatment, as well as "the measurement of live organisms in samples by qualified personnel with best available sampling and analytical methods" to verify the effective performance of the installed systems.

Additionally, national governments are providing requirements in this area, as well. Recently in the U.S., ballast water discharge regulations were enacted. Additional rules are expected in the future due to the seriousness and the nature of the problem. It is anticipated that new or improved methods will be required to increase detection limits sufficiently to statistically evaluate even higher standards. Multiple levels of government are involved in this complex issue. The Coast Guard, for example, is expected to issue create and enforce rules establishing more stringent discharge standards as research and analysis provide even greater support for these measures.

Existing ballast water treatment systems are not well developed and are restricted to use on land. Moreover, existing ballast water treatment systems have not been adequately verified, to provide certainty that the BWT systems are actually killing all live organisms in ballast water tanks. Indeed, shipboard methods to verify their efficacy in killing or eliminating all organisms in the ballast water are still needed. Although BWT systems can be tested in land-based locations to obtain approval prior to installation, ships vary greatly in the configuration of their ballast water systems, and this fact could affect the efficacy of any ballast water treatment system once installed. Moreover, the function of installed systems needs to be verified regularly to assure continued efficacy. What is needed is a comprehensive test regime that integrates land-based and shipboard testing, which will provide the best evidence that a BWT system will perform properly.

Applicants have discovered methods, systems and devices for testing water, including environment and ballast water, for biochemical evidence of living and/or dead organisms. Applicants have developed and tested a unique automated fluorescence live/dead biochemistry with water from a variety of sources, including, but not limited to, environmental and ballast waters. Applicants have discovered methods and developed apparatuses, devices and systems to verify the efficacy of land-based ballast water treatment systems in killing or eliminating all organisms in the ballast water. The automated, fluorescence-based methods of the invention provide a way to differentiate live organisms from dead organisms in water. The automated, fluorescence-based methods, and the apparatuses and devices provided herein, can be adapted to test for a particular organism or multiple organisms. As a non-inclusive example, the automated, fluorescence-based methods, and the apparatuses and devices provided herein, can be adapted to test for microorganisms, bacteria, yeast, algae, or specific organisms, including but not limited to, *E. coli, Salmonella* species, and any other species desired. Additionally provided are novel chemistries and novel controls for use in fresh, brackish and salt water systems and with fresh, brackish and salt water organisms. The technologies will be used to verify the efficacy of ballast water treatment methods. The systems of the invention are automated and enable self-testing, regulatory testing and regulatory enforcement, as well as automation of analysis of test volumes of all sizes, including but not limited to volumes larger than those able to be tested by current methods.

The invention provides methods and devices for monitoring and verification of the efficacy of treatments of ballast water from ships to decrease or eliminate the discharge of live organisms, to prevent the introduction or spread of non-native or pathogenic organisms.

The invention also provides methods and devices for use in monitoring microorganisms in recreational water, drinking water, runoff water, production water, waste water treatment facilities, health care environments, water for research, and the like. The devices and methods described herein can also be used to concentrate organisms for the extraction of metabolites (to provide components such as metals or minerals), nucleic acids (to provide, e.g., DNA or RNA), proteins, lipids, and the like.

In an embodiment, the methods and devices allow for automated monitoring and verification of the efficacy of treatments of ballast water from ships to decrease or eliminate the discharge of live organisms, to prevent the introduction or spread of non-native or pathogenic organisms.

In an embodiment, the methods and devices allow for automated monitoring and verification of viability testing of water, including ballast water, as well as recreational water, drinking water, agricultural water, waste water, and fluids from other environments, including but not limited to health care environments. In another embodiment, the automated monitoring can be done remotely, via internet connection, thus allowing for the monitoring to be performed at any desired location. Sample data generated using the methods, systems and devices of the invention can be sent to an operator or analyst or any interested party given access to the system within minutes of the completion of the testing.

In another embodiment, the filters used in the methods, devices and systems of the invention can be reusable. The filters can be replaced at any time, and are able to be reused to complete greater than 150 tests. Alternatively, instead of a single reusable filter, a manifold of filters can be used simultaneously to increase surface volume or water transferred from one filter to another after certain number of uses or if backpressure reaches a certain threshold. The later can delay the number of times a filter system or cassette would need to be changed manually, which thereby also reduce costs of frequent filter changes.

The devices, apparatuses and systems of the invention are comprised of components that are relatively easy to obtain and inexpensive. In certain embodiments of the invention, the devices, apparatuses and systems can be manufactured for less than $10,000 USD. In an embodiment of the invention, the devices, apparatuses and systems can be engineered into the ballast system of a ship or other craft, which eliminates the need for manual sampling.

Applicants have unexpectedly discovered that filtration in an automated device as described herein removes soluble enzymes in the fluid surrounding the organisms and concentrates the organisms so that the device can detect significantly lower and more meaningful (from a public health and verification of ballast water treatments perspective) concentrations of organisms.

The inventions differentiate live from dead organisms, which have been killed by a variety of methods such as heat, chlorine, or NaOH. The present invention provides filtration using various mesh sizes, and therefore, the methods and systems of the present invention can assess live organisms of different sizes. These types of methods, apparatuses and systems are applicable to many situations where aquatic or environmental monitoring is needed, required or mandated, including, but not limited to, ballast water.

The invention provides an automated method that is built on a platform that incorporates an automated filter capture and backwash system, which enables the detection of pathogens and organisms, including but not limited to *E. coli*, at concentrations of at least about 5×, or at least about 10×, or at least about 20× lower than existing devices. The present invention utilizes a substrate (FDA) that enables the detection of a broad range of organisms, including, but not limited to bacteria, phytoplankton, and zooplankton for water testing.

Provided by the invention is an automated device for accessing the viability of a wide range of organisms based on the metabolic production of fluorescent products from non-fluorescent substrates. Essential and unique components of the invention include, but are not limited to, the incorporation of a reusable filter to concentrate the organisms, the backflush of the filter to collect the organisms for assay, and the addition of the substrate in a fluorescent detection chamber to detect the enzymatic activity produced by viable organisms to detect the presence of such organisms.

While concentrating a sample can be useful in some embodiments, dense cultures or samples can also be diluted and then measured. For example, probiotic production facilities often need to carefully monitor the numbers of organisms per volume of media. Thus, for example, a 0.1 mL sample can be diluted into 100 mL and then processed according to the methods described herein.

In an embodiment of the invention, all valves and pumps are controlled by computer or microprocessor. In another embodiment of the invention, some of the valves and pumps are controlled by computer or microprocessor. In an embodiment of the invention, sensor responses are recorded by computer or microprocessor.

Applicants have unexpectedly discovered that the use of filtration solves a number of problems existing in known or pre-existing devices, systems and methods: (1) filtration enhances sensitivity of detection by concentrating organisms from a large volume of fluid into a significantly smaller volume and (2) filtration allows the removal/exchange of the extracellular medium in which the organisms were collected in in order to remove any extracellular enzyme that may have been present, and (3) filtration provides for the immersion of the organisms in a buffer that gives consistency from sample to sample.

Applicants have also discovered that the automation and the use of reusable filters enable the devices, systems and methods of the invention to be used by operators with very little training or skill, as well as any other operator. The robustness provided by the automation and reusable filters provides greater compliance in the field, and greater buy-in by ship owners, ship builders, and ship hands.

The devices, methods and systems of the invention provide a new combination of pre-existing components. The new combination of the components solves problems encountered in the operation of other devices regarding sensitivity or rapidity of measurement, skill involved in use, and possibility of permanent installation of viability testing devices with new ballast water treatment systems.

The devices, methods and systems of the invention have a number of water-testing applications, including, but not limited to, the following:

The devices, methods and systems of the invention can be installed or utilized as one or more permanent accessories of ballast water treatment systems to verify the efficacy of the treatment systems in killing a broad range of organisms. When used in this way, the invention provides for the substrate to be a non-fluorescent substrate that can be converted to a fluorescent product by a wide-range of esterases found in virtually all organisms. A non-limiting example of such a substrate is fluorescein diacetate (FDA). As discussed above, the product of esterase activity is the highly fluorescent chemical fluorescein. Other substrates, with similar broad ranges of esterase sensitivity, are also able to be used in a similar fashion.

The devices, methods and systems of the invention can be used for testing of ballast water treatment systems in which a measurement of the amount of *Escherichia coli* is desired. In such applications, a non-fluorescent substrate of beta-gluuronidase (an enzyme that is relatively specific for *E. coli*) that produces a fluorescent product can be used. Several such compounds are known and have been used in many assays of *E. coli*. Similarly, non-fluorescent substrates for enzymes that are relatively specific for *Enterococcus* and produce fluorescent products can be used for detection of *Enterococcus*. Measurements of both *E. coli* and *Enterococcus* are particularly criteria for evaluating efficacy of ballast water treatment systems in regulations of a provisional treaty of the International Maritime Organization (IMO) that is often cited in various U.S. and state ballast water regulations.

The devices, methods and systems of the invention can be used for testing recreational water (e.g., at beaches, in rivers and lakes and the like) for safe human or animal contact. The devices, methods and systems of the invention can be used for measuring viable *E. coli* or *Enterococcus*, if given the appropriate non-fluorescent substrate, or for any other organism of interest and given the appropriate non-fluorescent substrate. The United States Environmental Protection Agency, as well as state regulations, requires water to have low levels of these organisms in fresh water or seawater, respectively. The devices, methods and systems of the invention would enable relatively unskilled operators to make assessments of the levels of these organisms in less than one hour. The ability to complete the assessment in such a short period of time is greatly beneficial to the improvement of the assessment of recreational water safety over current methods, which are culture-based and generally take >18 hours to measure criterion levels of these respective organisms.

FDA has previously been used as an organismal marker to detect live organisms using microscopic analysis. The detection and counting of such organisms is a labor intensive task required skilled biologists to differentiated organisms from debris among the dead and detritus of aquatic samples. The fluorescence in the organisms fades quickly, most likely due to leaking of the fluorescent product fluorescein out of the live organisms.

Provided herein are devices, systems and methods for automated live/dead measurement of organisms. The devices, systems and methods provided herein utilize, in part, the fluorogen fluorescein diacetate (FDA). The technology provided herein enhances the ability of treatment systems, including, but not limited to ballast water treatment systems, to handle large volumes of water and to detect low concentrations of organisms. The inventions provided herein may be used in a variety of locations, and in a variety of ways, including but not limited to on land and on ships, vessels and/or vehicles.

In addition to general live-dead testing of water organisms, the devices, methods and systems provided herein can also be used with other chemical substrates for rapid automated testing for bacteria, such as *E. coli*. The devices, methods and systems provided herein provide at least about a 5-fold increase in sensitivity at detecting microorganisms and/or bacteria, including *E. coli*. The devices, methods and systems provided herein provide at least about a 10-fold increase in sensitivity at detecting enabling detecting microorganisms and/or bacteria, including *E. coli*. The devices, methods and systems provided herein provide at least about a 10-fold increase in sensitivity at detecting enabling detecting microorganisms and/or bacteria, including *E. coli* in recreational and ballast water detection of *E. coli* at criterion level in less than one hour. In addition to being valuable for assuring low levels of *E. coli* in ballast water (an important ecosystem result and a recommended IMO test), this automated rapid test for *E. coli* could be used for water monitoring of all kinds, including but not limited to beach water, drinking water, effluent water, resulting in a significant impact in protecting the health of entire ecosystems and environments, as well as animals, including humans.

The invention provides a fully automated system for viability testing of organisms in aquatic systems, including, but not limited to, ballast water.

The invention provides an automated device that can assess viability of a wide range of organisms based on the metabolic production of fluorescent products from non-fluorescent substrates. The device provided herein utilizes one or more reusable filters to concentrate the organisms, followed by the backwashing of the filter to collect the organisms for assay, an addition of the substrate in a fluorescence detection chamber to detect the fluorescent product of enzymatic activity that is produced by, and leaks from, viable organisms to detect the presence of such organisms.

The filtration backwash is a quantitative method developed by Applicants for DNA-based live-dead technology in ballast water, in order to enhance sensitivity by concentrating organisms from a large volume of fluid into a much smaller volume. The procedure removes residual ballast treatment chemicals and extracellular enzymes and enables immersion of the organisms in a buffer that provides consistency from sample to sample. Automation enables device and systems of the invention to be used by operators of a broad range of skills—from relatively unskilled operators to highly skilled operators. Another feature of the invention is that automation enables the devices and systems of the invention to function as installed components of a ballast water treatment system.

Thus, the invention provides analysis and measurements of live or dead organisms, for example, using FDA. However, other agents can be used to measure organisms such as *E. coli*. For example, various other dyes, fluorescent molecules, enzymes and/or substrates can be used to measure total organisms, gram positive organisms, and the like. The measurement of organisms can be used for analysis of invasive or pathogenic species. However, the technology can also be used to assess any population of microorganisms, for example, to assess population growth, stasis, or decline. The devices and methods described herein can be used to track growth history over time, determine if populations meet regulatory requirements, track population dynamics, measure secondary environmental/ecological influences, and the like.

The invention provides system and device designs of varying specification and features, including varying degrees of: automated control; number of values; diameters of filters, tubes, and cuvettes; numbers of filters. The fully functional, automated live-dead testing devices and systems of the invention contain completely integrated components. Additionally, devices and systems of the invention are tested over duty cycles from short duration (less than one minute) to very long duration (greater than 72 hours), and under varying temperature conditions.

The devices and systems described herein have been optimized for fluorescence sensitivity so that the results can be validated by comparison to currently accepted methods in the ETV protocols and standard or recommended practices. The detection system of the devices and systems of the invention can be an expensive fiber optic spectrometer, for the purpose of providing quantitative resolution to fractions of nm of wavelength, as well as less expensive solid state light sensors, color filters, and microfluidic sampling, depending on the conditions under which they will be used.

In one embodiment, the spectrometer is a sophisticated, fiber optic device. In an embodiment, the spectrometer samples the fluorescence in a small cross-section of the 3 mL cuvette in which the results are assayed to measure a relatively simple variable: the amount of fluorescent light in a small range of wavelengths. The invention optionally provides alternative sensor configurations and applications. In another embodiment, the invention provides increased sensitivity and decreased cost by utilizing avalanche photodiodes and compact photomultipliers. These can be combined with compact micro-optics to integrate light from the entire cuvette or from microfluidic sampling channels. In another embodiment, the fluorescence is photographed with a digital camera having very low light sensitivity capability and the intensity of the recorded light is analyzed by software. Fluorescence excitation may be provided by low-cost light emitting diodes (LEDs) operating in pulsed mode for ambient light cancellation. Low cost gelatin films can be used optionally, in place of traditional optical filters, and this embodiment of the invention provides further cost reduction. The invention provides a decreased cost of fluorescence sensing by 5-10 fold (from thousands to hundreds of dollars), while also improving the sensitivity.

Figure 7:
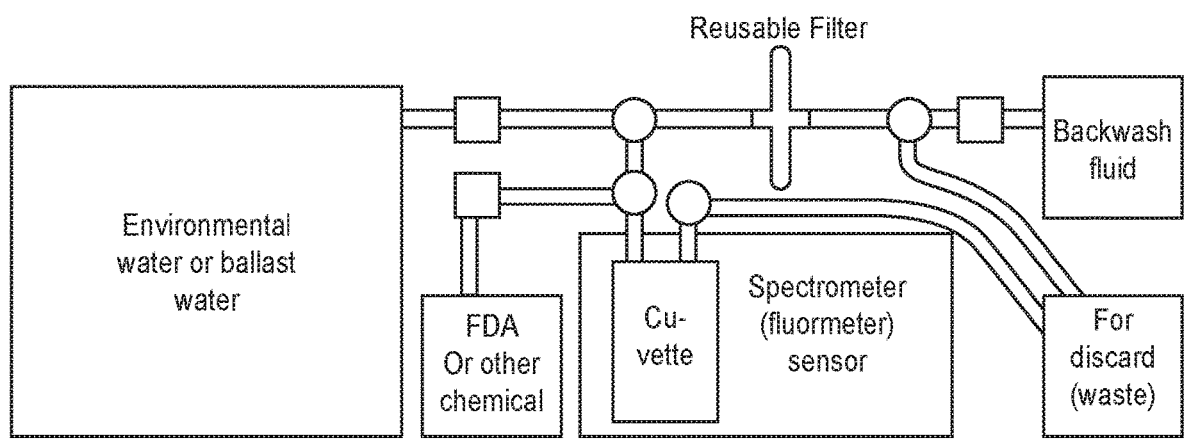
FIG. 7 provides a schematic of automated ballast water analysis device. Pumps (squares) are KNF Neuberger, PML3194NF-11; valves (circles) are Gems Sensors, B3317-S20.
Figure 8:
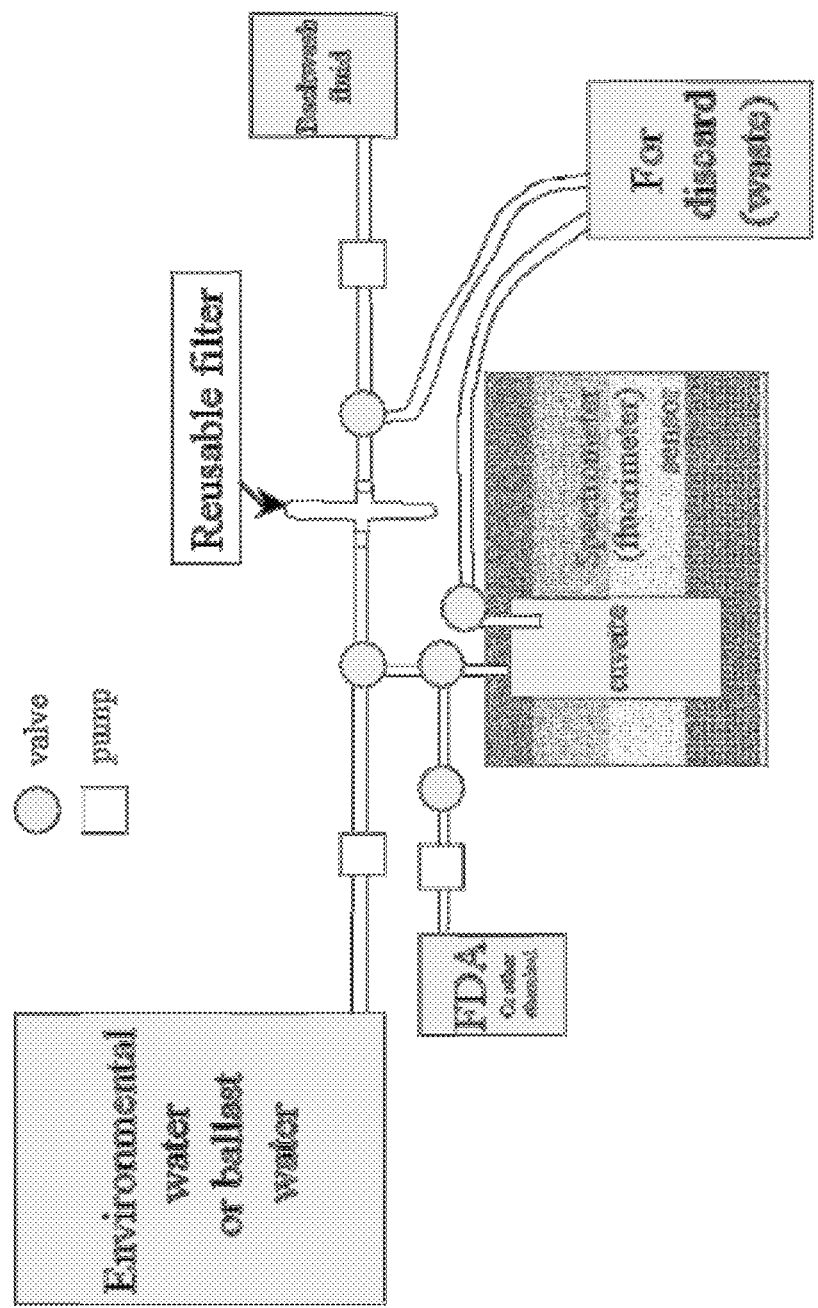
FIG. 8 provides another schematic of automated ballast water analysis device, containing an additional valve. Pumps (squares) are KNF Neuberger, PML3194NF-11; valves (circles) are Gems Sensors, B3317-520.
Figure 9:
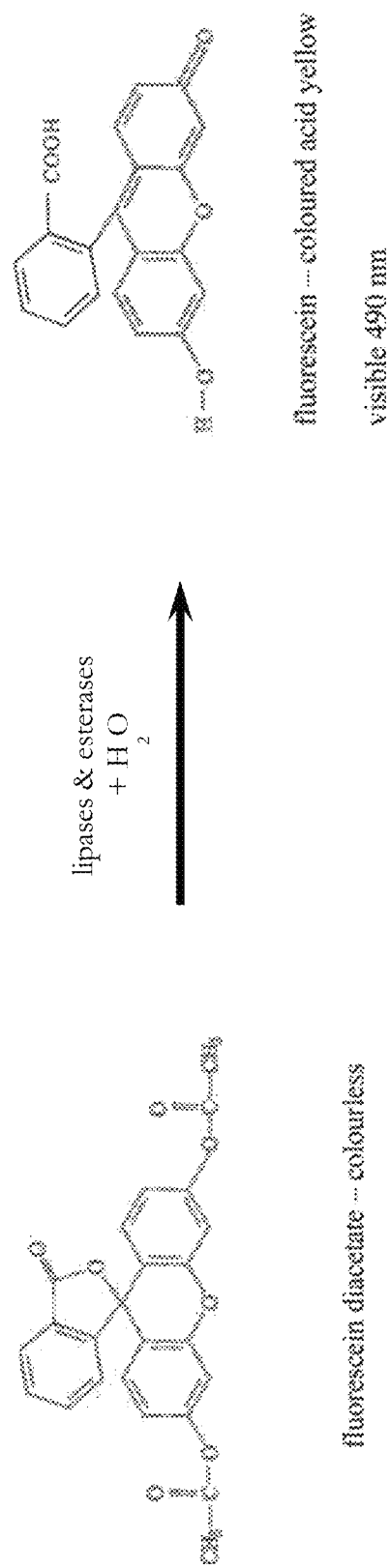
FIG. 9 illustrates the hydrolysis reaction of fluorescein diacetate to produce fluorescein.
Figure 10:
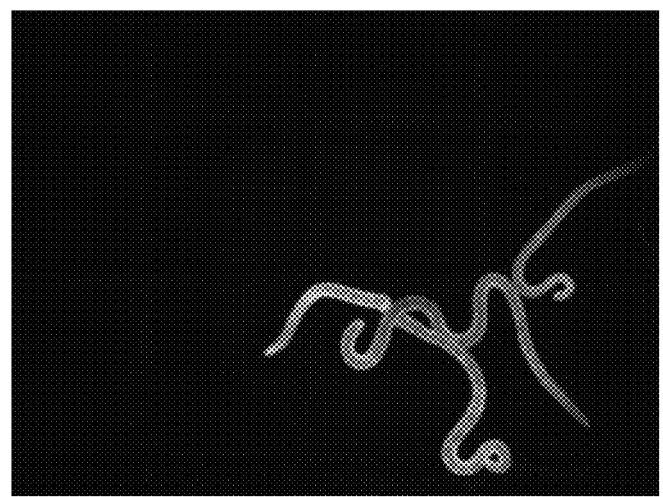
FIG. 10 illustrates live organisms showing fluorescence emissions (peak ~520 nm).
Figure 11:
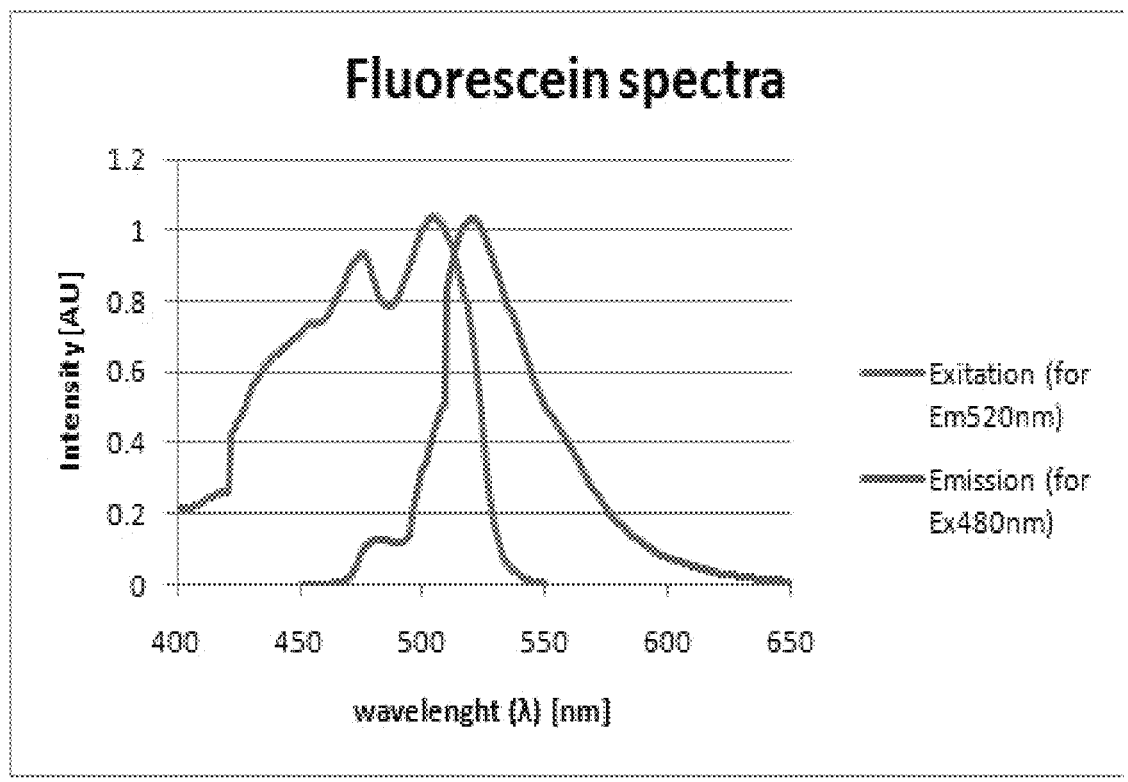
FIG. 11 provides a graph depicting the optical absorption measurement of Fluorescein and the fluorescence emission spectrum of Fluorescein.

One embodiment of the invention is illustrated in FIG. 7. FIG. 7 shows a simplified version of the device of the invention. In this design, environmental water is pumped onto a filter (0.2 µm filter, 10 µm mesh, or 35 µm mesh which has 50 µm diagonal size); valves are switched to backwash the material captured on the filter/mesh into the reaction/detector cuvette, containing a buffered solution; stock FDA is added from a reservoir/pump/valve, and a spectrometer measures fluorescent product produced by viable organisms over time. FIGS. 7 and 8 provide non-limiting examples of the device, which show one filter. However, the devices, systems and methods of the invention provide for one or more filters. For example, certain separation functions require greater than one filter.

As used herein, fluorescence is the emission of light by a substance that has absorbed light or other electromagnetic radiation. It is a form of luminescence.

As used herein, a fluorometer or fluorimeter is a device used to measure parameters of fluorescence. A fluorimeter measures the intensity and wavelength distribution of the emission spectrum after the excitation of molecules by a certain spectrum of light. These parameters are used to identify the presence and the amount of specific molecules in a medium.

Figure 2:
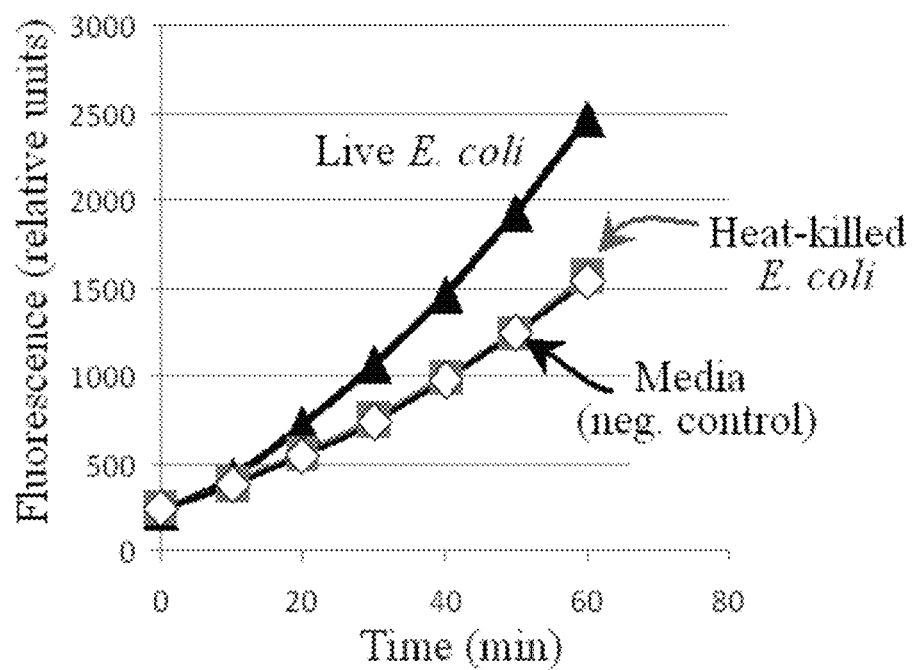
FIG. 2 illustrates the increase in FDA-containing media fluorescence in presence of live *E. coli*, compared to dead (heat-killed). *E. coli* or sterile water (media was 60 mM PB, pH 7.6).

As used herein, a fluorogen is a nonfluorescent precursor of a fluorophor, which is a fluorescent molecule. Fluorescein diacetate (FDA) is a fluorogen, i.e., a non-fluorescent chemical that yields a highly fluorescent product, fluorescein, in response to numerous enzymes (esterases, lipases, etc.) active in live organisms but not dead ones (FIG. 1). Enzymes in live organisms hydrolyze fluorescein diacetate into highly fluorescent fluorescein. Once an organism dies, the enzymes are rapidly degraded, and thus the ability of the enzymes to hydrolyze fluorescein diacetate is greatly decreased. It has been shown that fluorescein brightly stains live organisms but not dead ones (FIG. 1) and is also produced by live bacteria exposed to FDA (FIG. 2). When FDA is in a liquid environment or media that also contains living organisms, the organisms metabolize the FDA and the resultant fluorescein leaks into the surrounding media. As provided herein, the leaked fluorescein can be measured fluorometrically with great sensitivity. This method of measuring leaked fluorescein also works well with phytoplankton (FIG. 3) and other organisms.

Measurement of fluorescence is a technique well-known in the art, and requires excitation of a fluorophore with electromagnetic waves (typically ultraviolet or visual light) having a shorter wavelength than the fluorescent emission from the excited fluorophore. The excitation and fluorescence wavelengths are specific for each fluorophore, and the skilled person will know how to choose suitable wavelengths for both purposes.

The measurement of fluorescein, the fluorescent product of FDA metabolism, in the fluid surrounding cells, has been used for indirect measurement of amounts of bacteria in soil samples (see, for example, Adam and Duncan, Soil Biology & Biochemistry 33 (2001) 943-951). The procedure described by Adam and Duncan involved extraction of the fluorescein from the surrounding fluid by solvents and did not use filtration to concentrate bacteria in the samples. It should be noted that the use of solvents in ecosystems, particularly aquatic ecosystems, is considered detrimental to the ecosystem itself.

The chemistry and concentrations of the dyes and buffers used in the devices, systems and methods of the invention are optimized. Prevention of false positives is critical for the methods, systems and devices of the invention. In some buffers (e.g., PB at pH 7.6, FIG. 2), abiotic production of fluorescein could give false positive results. Caution must be used so that buffering agents do not kill the organisms, in order to avoid false negative results. The invention provides the use of varying buffers and other fluorogens to decrease abiotic background and increase signal to noise performance. Because the rate at which fluorescence develops is dependent on fluorogen concentrations, there must be consideration given to the balance between speed and cost of the fluorogen.

The filter or filters used in the invention will normally have a pore size small enough so as to retain substantially all contaminants in the medium. That is, all contaminants of interest. In embodiments of the present invention where it is only of interest to prepare the sample to allow detection of certain contaminants (e.g. not the above-mentioned fragments of bacteria, fungi or spores) the pores can be set to a size that will allow such contaminants to pass through the filter. However, since there are large differences between e.g. protozoan cells and certain bacteria, the pore size of the filter can vary. Also, in order to "catch" contaminants having defined sizes, the method described herein can be run in several parallel tracks, each using its own pore size in step a; for example, simple subtraction of two measurements obtained from different pore sizes will provide information of the presence of contaminants having a size in the interval between the two pore sizes. Consequently, it is preferred that the pore size is at most 20 µm, such as at most 15, at most 10, at most 5, and at most 3 µm. For retaining spores or fragments of microorganisms, even smaller pore sizes are preferred, including, but not limited to 0.2 µm or 0.22 µm.

Furthermore, the pore size should be large enough to let the detectable moiety pass through the filter; this is of essence when a subsequent detection is performed on the liquid medium which has been evacuated by forcing it through and away from the filter. In this context, the pore size is at least 0.1 µm (but may be larger such as at least 0.22 µm or at least 0.45 µm), but again, the suitable pore size depends on the choice of detectable moiety.

The at least one substrate used according described herein may conveniently produce the detectable moiety by being cleaved (or otherwise chemically converted) by an enzyme that is characteristic for the contaminants. By this is meant that the enzyme in question is biochemically active in the contaminants that it is the objective to determine. It should be borne in mind that the present invention allows for both detection of total contamination and for detection of contamination with certain subsets or species of contaminants. In the first case, it will be convenient to use a substrate that is converted by a phylogenetic ally preserved enzyme, i.e. an enzyme or enzyme activity that exists in highly homologous form in practically all contaminants of biological origin, i.e. in most living or viable microorganisms. In the latter case, it will be convenient to use a substrate that is converted by an enzyme that is highly specific for the relevant contaminants. At any rate, the enzyme is typically selected from the group consisting of carbohydrates, proteases, lipases, esterases, amidases, sulfatases, nucleases, and phosphatases such as alkaline phosphatase.

The enzyme that processes the substrate can be expressed constitutively by microorganisms, phytoplankton, and/or zooplankton. This has the advantage that induction of enzyme production in the contaminants should be unnecessary. It is further relevant to point out that induction of enzyme activity could be a source of error and uncertainty because control over the induction might be difficult to achieve.

Hence, enzymes that can be used in the methods described herein include those naturally produced in living cells. Detectable enzymatic activities can be activities that are expressed constitutively, expressed in all growth phases of the microbial target population/bacteria/phytoplankton/zooplankton and/or expressed independently of the physiological state of the microbial target population/bacteria. The enzymatic activity may be intracellular and/or extracellular. The methods, systems and devices can thus include the detection and quantification of an enzymatic activity selected from enzymes hydrolyzing substrates providing essential nutritional elements for the growth of the target microbial population/bacteria. In the present context the expression "essential nutritional elements" indicate nutrients as defined in e.g., Brock et al., Biology of Microorganisms, Prentice-Hall, Inc., Englewood Cliffs, N.J., USA. Thus essential nutritional elements include nutrients, without which a cell cannot grow and include macronutrients as well as micronutrients.

Accordingly the present method can be based upon detection of a microbial/bacterial enzyme involved in e.g., carbohydrate, protein, and phosphate and sulphate metabolism. An embodiment of the method is detection of microbial phosphatase enzymes. In particular it is interesting to detect alkaline phosphatase involved in phosphate metabolism including the hydrolysis of phosphate esters, including esters of primary and secondary alcohols, sugar alcohols, cyclic alcohols, phenols and amines, liberating inorganic phosphate. The enzyme also hydrolysis polyphosphates $PP_1$ and the transfer of a $PO_4^{3-}$ group from $PP_1$ (and from a number of nucleoside di- and triphosphates and from mannose-6-phosphate) to glucose, forming glucose-6-phosphate. The alkaline phosphatase activity measurements according to the present invention provide a robust measurement of microbial numbers.

Preferred substrates are fluorogenic or chromogenic substrates producing blue, green and red products (fluorescent or luminescent etc.) as the detectable moiety. Detection of light emission is a highly convenient and fast way of obtaining information of the presence of relevant moieties. Useful substrates in this context are disclosed in Molecular Probes: Handbook of fluorescent probes and research products, ninth edition, author: Richard P. Haugland, chapter 10, pages 397-448, which is incorporated by reference herein.

Substrates selected from the group consisting of 5-bromo-4-chloro-3-indolyl phosphate disodium salt; 9h-(1,3-dichloro-9,9-dimethylacridine-2-one-7-yl) phosphate ammonium salt; fluorescein diphosphate tetraamonium salt; a methylumbelliferyl derivative such as 6,8-difluoro-4-methylumbelliferyl phosphate, 4-methylumbelliferyl phosphate dicyclohexylammonium salt trihydrate, 4-methylumbelliferyl phosphate free acid; 4-methylumbelliferyl phosphate dilithium salt, 4-methylumbelliferyl-β-N-acetylglucosaminide, and trifluoromethylumbelliferyl phosphate; salts of 4-nitrophenyl phosphate; and resorufin phosphate may also be used in the methods, systems and devices of the invention.

The detectable moiety should preferably be detectable in an amount of at the most 100 picomoles, preferably at the most 50 picomoles, more preferably at the most 20 picomoles and even more preferably at the most 10 picomoles and most preferably at the most 1 picomoles. The lower the detection limit is for a particular selectable moiety, the higher the sensitivity is for the method.

According to the invention, it is possible to use one single substrate, but it is also possible to use at least two substrates that produce detectable moieties providing signals that can be combined into one single measured signal value. By this is meant that the signal obtained from these moieties can be measured within the same measurement window and therefore be integrated into one single measurement (a simple example would be that the moieties are identical even though they originate from conversion of different substrates with different enzymes). Thus, this is a practical means for obtaining information on the total contamination in the sample, especially in the cases where it is not feasible to use one single substrate in order to obtain this information.

It is also possible to use at least two substrates that produce detectable moieties providing distinguishable signals. This provides the advantage that several different groups of contaminants can be determined individually.

In order to obtain a reliable measurement of viable microorganisms, the above-mentioned substrates should therefore be selected so as to use those that are converted by enzymes characteristic of viable microorganisms. One example could be a constitutively expressed enzyme having a high turnover in a metabolically active microorganism.

In the practice of the invention, it is desirable that the amount of substrate in the liquid vehicle does not limit the rate of production of the detectable moiety, since this has the consequence that only the amount of converting enzyme (and hence the amount of contaminants) will set the rate of production. Typically, the substrate/enzyme combination will be chosen so as to ensure that the rate of production of the detectable moiety is a function (preferably linear) of the quantity of contaminants in the known volume of the medium.

In many cases it will be relatively simple to ensure that the amount of detectable moiety which is produced can be translated into a "contaminant number". It may e.g. suffice to provide a qualitative result (of the type "contamination" or "no contamination") because it is merely of interest to determine whether or not a certain threshold value has been exceeded. In other cases, knowledge of the sample type and the system from where it is derived will ensure that one single pass of the methods, systems of devices of the invention provides for a precise determination of the contamination count.

The period of time referred to in step c is the time interval which allows formation of sufficient amounts of the detectable moiety so as to render detection thereof possible. This time interval is conveniently less than 24 hours, but normally much shorter, such as at the most 12, 11, 10, 9, 8, 7, 6, 5, 4, 3, 2, and 1 hours. Normally the time interval will not be less than 5 minutes and it is in most cases not less than 20 minutes.

In embodiments of the present invention, the filter is part of a closed, sterile filter assembly. The sterility of the filter assembly ensures that it will not affect the signal to noise ratio in a subsequent measurement, because it does not contribute with contaminants itself. The closed nature of the device serves the same purpose, but also adds to the ease of use of the method of the invention, because the filter unit facilitates easy, practical and sterile handling of the sample.

Filters suitable for use in the methods, system and devices of the invention include commercially available as well as custom made filters, ranging in pore size from 0.2 μm to at least about 50 μm or greater. The filters for use in the methods, system and devices of the invention can be made of cellulose acetate (Thermo Scientific #190-2520) or other suitable material for the conditions. Despite repeated wash/reuse cycles, reproducibility of both clean cycle and test cycle measurements have been shown. Nylon mesh with larger pore sizes is typically reused more times than 25 times in conditions such as in plankton nets. The methods, systems and devices of the invention provide for repeated wash/reuse cycles, ranging from at least 10 cycles to 25 cycles to 100 cycles to 250 cycles to greater than 500 cycles. Length of time for filter use is also optimized in the invention. The methods, systems and devices of the invention provide for repeated wash/reuse cycles over a period of time ranging from less than 1 day to 1 month, to 4 months, to 6 months, to 10 months, to 1 year, and up to 5 or more years. Filters and mesh holders are designed to be serviceable for replacement when needed and optimized for volumes and timing for sample application, as well as wash solutions between samples and effect of temperature on the filter.

The methods, systems and devices of the invention are designed to monitor, reduce or eliminate the formation of biofilms on the filters. In any filter system, the formation of biofilm can lead to false positives and potential filter blockage. The invention provides systems, methods and devices wherein the filter component is able to be reused many times. The methods, systems and devices of the invention are designed to suppress and remove biofilm with agents, including but not limited to lysis agents previously employed in microfluidic devices. See Balagadde et al., 2005.

The methods, systems and devices of the invention are designed to withstand high levels of organisms or turbidity, thereby allowing filtration of the desired volumes and maintaining the robust characteristics required for use. As a non-limiting example, environmental source waters having E. coli counts exceeding 2000 cfu/100 mL have been tested in the devices of the invention. The methods, systems and devices of the invention are designed to monitor pressures and flow rates in order to prevent device, system or method failures. Devices of the invention optionally include flow and pressure sensors, and other sensors as needed, pressure gauges, temperature gauges, and electronic feedback control to maintain desired parameters in desired ranges. Additionally, the devices of the invention optionally include gauges to monitor filter, valve and pump function. Flow sensors provide for control of the total volume being assayed. For example, ballast water regulations contain language regarding the density of organisms, and therefore, the volume of water assayed must be taken into account when selecting the proper method, system or device of the invention for this use. The methods, systems and devices of the invention provide for a large variety and range of backpressures and pump rates, which allow the user to determine the best flow rates and pressures for system operation and reproducibility.

The methods, systems and devices of the invention can use a simple, manual software interface supplied with the relay control board to control the pumps and valves, or, optionally, a sophisticated automated software interface, including an interface designed for a specific use or situation. According to the invention, data from the spectrometer is automatically uploaded into spreadsheet, which is analyzed via software, or may be analyzed manually, if needed. The sophisticated automated interface provides the advantages of both feedback control and real-time analysis. In an embodiment of the invention, an embedded solution with an on-board microcontroller, integrated electronics, compact power supply, and a generic USB connection to a tablet PC is utilized, which can serve the needs of cost containment and size constraints.

Data acquisition cards and software from suppliers such as Labview (National Instruments may be used to provide an easy-to-use graphical user interface. Furthermore, the system can be an embedded solution with an on-board microcontroller, integrated electronics, compact power supply, and a generic USB connection to a tablet PC.

The invention provides methods, systems and devices for the separation and capture of multiple sizes and classes of organisms, including a 35 µm mesh for capturing organisms >50 µm in size (the diagonal length of the 35 µm mesh, the flow-through from stage 1 captured on a 10 µm mesh, and stage 3, remaining organisms captured on an 0.2 µm filter. The invention provides methods, systems and devices for filtering larger volumes through larger mesh sizes due to regulations which require detection of smaller densities of organisms in greater volumes. In this example, part of the "flow through" is diverted out of the apparatus; only part of the "flow through" is filtered through the next smaller filter size. The invention provides methods, systems and devices with automated sampling and assay, and therefore, any particular size category can be captured on its appropriate mesh or filter and assayed multiple, repeated times.

The devices, systems, methods and apparatuses provided herein may be used in conjunction with any of the devices, systems, methods and apparatuses of the invention. Certain devices, systems and apparatuses provided are contemplated to be used to detect, measure or detect and measure the live/dead organisms in a fluid sample. Additionally, certain devices, systems and apparatuses provided are contemplated to be used to enhance systems, devices and apparatuses for the detection and/or measurement of live/dead organisms in a fluid sample.

Provided is an injection apparatus, for injecting a substrate used to detect the presence of living organisms in a fluid, where the apparatus includes a syringe reservoir, a syringe pump, an electronic rotary valve, and a controller. Additional components may be used with the apparatus, depending on the use or results needed.

Further provided is an injection apparatus for injecting the substrate used to detect the presence of living organisms in the test fluid. The reservoir of the injection apparatus can contain a predefined volume of substrate and can be discarded and replaced once empty. Optionally, a desired volume of substrate can be added to the reservoir on site or at a remote location. The syringe pump of the injection apparatus is used to aspirate the substrate from the reservoir and dispense the substrate into a cuvette. The electronic rotary valve of the injection apparatus may be used to change the flow path of the substrate, either from the reservoir to the syringe or from the syringe to the cuvette. The controller of the injection apparatus includes, but is not limited to, a microcontroller or similar component. The controller of the injection apparatus controls the rate of dispensing and aspiration of the substrate by the syringe pump and controls the valve.

Additionally, provided is a thermo-regulation apparatus for regulating the temperature of the substrate used to detect the presence of living organisms in a test fluid, including a heat conductive housing which encloses the reservoir and syringe of the injection apparatus as well as a temperature sensor, a heat pump, a material for dissipating heat, and a controller.

The thermo-regulation apparatus for regulating the temperature of the substrate used to detect the presence of living organisms in a fluid, such as a test fluid, includes a first heat conductive housing, which can enclose the substrate reservoir and syringe of the injection apparatus and the temperature sensor, where the temperature sensor is situated directly on or connected to the heat conductive housing via a second heat conductive material, where the heat conductive material can be the same or a different heat conductive material as the first heat conductive material, a heat pump, where the heat pump is a thermoelectric heat pump and said heat pump is positioned in direct proximity to, or directed on, or connected to the housing in the injection apparatus via a second heat conductive material, a heat dissipation material located directly on or connected to the thermoelectric heat pump via a third heat conductive material, and a programmable microcontroller, which controls the rate and duration of the heating and cooling of the thermoelectric heat pump, based on values recorded by the temperature sensor.

The heat conductive material used for the first, second and third heat conductive material may be the same heat conductive material, or may be different, depending on the results sought, the conditions under which the thermo-regulation apparatus will be operating, availability of materials, or for any other reason.

Further provided are sensors, which detect the presence of living organisms in the cuvette. A representative sensor comprises a first LED, a photodiode, an emission filter, a LED driver, a second LED, a temperature sensor, and a microcontroller.

In certain embodiments, the sensor comprises a first LED, which is used to emit the excitation wavelength of the substrate, a photodiode, for the purpose of detecting the emission wavelength of the substrate, an emission filter which attenuates all wavelengths of light from the cuvette except for that of the substrate before detection by the photodiode, a LED driver having the capacity to process a pulse width modulated signal, a second LED, where the second LED has the same emission wavelength as that of the substrate and is used to calibrate the sensitivity of the photodiode, a temperature sensor, which measures the temperature of the photodiode, a microcontroller capable of outputting a pulse width modulated signal to the LED driver, controlling the frequency of detection by the photodiode and generating a temperature compensated output of the fluorescent intensity of the substrate.

The sensors of the invention can be used to detect the presence of living organisms in fluid. The sensors of the invention can be used to detect the presence of living organisms in a cuvette or other container used in a manual or automated device for accessing the viability of organisms in a sample, such as ballast water. Optionally, the sensors of the invention are cushioned. The function of the cushion is to reduce effects of vibration on the sensor.

Also provided is an apparatus for regulating the temperature of the sensors of the invention. The apparatus for regulating the temperature of a sensor, as provided above, comprises a first heat conductive housing, which encloses the cuvette and said sensor, and a heat conductive material connecting the first heat conductive housing to the heat conductive housing of the thermo-electric regulation apparatus. Other embodiments of the apparatus for regulating the temperature of the sensors of the invention include, for example, a thermoelectric heat pump attached to a heat dissipation material that is attached directly to the first heat conductive housing.

Provided is a method of preparing a backflush solution, comprising filtering an amount of a test fluid, wherein the filtration removes all organisms from the test fluid, placing the filtered test fluid into a holding container, adding an amount of a buffer to the filtered test fluid, titrating the test fluid with an amount of an acid or a base to achieve the desired pH.

In a non-limiting example, the prepared backflush solution is used in an automated device for detecting contaminants.

Additionally, provided is an apparatus for preparing a backflush solution, comprising a syringe filter, one or more holding containers, wherein each holding container has a plurality of ports, a pump, an electric rotary valve, a solution mixing device, one or more syringe pumps, one or more flow meters, a pH sensor, and a microcontroller.

In an embodiment, the apparatus for preparing a backflush solution comprises a syringe filter. In another embodiment, the apparatus for preparing a backflush solution comprises a syringe filter having a pore size of 0.2 µm.

Provided is an apparatus for preparing a backflush solution, comprising a syringe filter, wherein the test fluid passes through the syringe filter, said filter removes microorganisms and other impurities from the test fluid, one or more holding containers, wherein each holding container has a plurality of ports, including but not limited to ports for the filtered test fluid, acid, base, buffer, pH electrode, and ejection of air inside the container, wherein the backflush solution is prepared in a holding container, a pump, wherein the pump draws the test fluid through the syringe filter in a holding container and forces the prepared backflush solution through the syringe filter, an electric rotary valve, wherein the rotary valve directs the flow and path of the filtered test fluid, acid, base, buffer, and the prepared backflush solution, a solution mixing device, comprising a rotating magnet outside and under the holding container and a magnet inside the holding container, one or more syringe pumps, wherein the syringe pumps inject acid or base into the holding container, one or more flow meters, wherein the flow meters determine the volume of fluid in a holding container, a pH sensor, wherein the pH sensor determines the pH of the filtered test fluid prior to, and following each addition of acid or base into the test fluid, and a microcontroller, wherein the microcontroller controls or monitors or controls and monitors the to control or monitor the pump, the rotary valve, the solution mixing device, the syringe pumps, the flow meters, and the pH sensor.

An apparatus for concentrating organisms of a selected size range from a test fluid, comprising one or more syringe filters, an electrical rotary valve, a programmable microcontroller, a mechanical coupler, said coupler attaches a stepper motor or servo to a manual rotary valve, The apparatus for concentrating organisms of a selected size range from a test fluid, wherein the syringe filters concentrate organisms in a selected size range. The apparatus for concentrating organisms of a selected size range from a test fluid, wherein the electrical rotary valve has an input for the test fluid and a plurality of outputs, wherein output connects to a syringe filter with a different pore size. The apparatus for concentrating organisms of a selected size range from a test fluid, wherein the programmable microcontroller operates the direction of fluid flow through the rotary valve. The apparatus for concentrating organisms of a selected size range from a test fluid, wherein the coupler attaches a stepper motor or servo to a manual rotary valve. The apparatus for concentrating organisms of a selected size range from a test fluid, wherein the rotary valves are controlled by a stepper motor, and further wherein the rotary valves only draw power when the stepper motor moves the valve from one position to another. The apparatus for concentrating organisms of a selected size range from a test fluid, wherein the manual rotary valve to which the stepper motor is attached by the mechanical coupler has a plurality of ports. In a non-limiting example, the some of the ports are opened and some of the ports are closed or blocked by positioning the axel of the valve in one of many rotary positions.

In certain embodiments, it can be advantageous to utilize rotary valves in the apparatuses of the invention, instead of solenoid-operated valves, because rotary valve require less power to operate, and enable a greater number of ports to be connected or disconnected. Typically, solenoid-operated valves have three ports and two states: either state one normally open between two of the ports or state two normally closed; the third port is correspondingly normally closed in state one and normally open in state two. To change from one state to another requires power input to the solenoid and the solenoid requires a continuous supply of power in order to hold the valve in the second state. Rotary valves do not require power to maintain second states, and can also be positioned to open or close more than three interconnected ports, which can be beneficial for many applications and situations.

Also provided is an apparatus for switching to onboard battery power, comprising a manual switch, a line voltage monitor device, a plurality of electrical relays, a programmable microcontroller. In the above-disclosed apparatus, the manual switch is used to toggle between battery power and external power. Also in the above-disclosed apparatus, the electrical relays toggle between sources of power, such as between battery power and an external source of power. In the above-disclosed apparatus, the programmable microcontroller triggers an electrical relay to switch to battery power if the line voltage monitor device detects a change in line voltage, such as a decrease in line voltage, the loss of line voltage or the absence of external sources of electricity.

Any of the devices or apparatuses herein may further comprise a programmable Wifi, ethernet or gsm connection, wherein the microcontroller of said device or apparatus can be remotely controlled, and wherein data from said apparatus or device can be retrieved. Any of the devices or apparatuses herein may further comprise a means, such as a Bluetooth connection, for recording and collecting communications with the treatment cycle and other behavior.

In the apparatuses and devices of the invention, rotary valves can automatically reset to home position. Additionally, the rotary valves can turn to pre-programmed positions for fluids to flow through specific ports under control of a programmable microcontroller. If a power outage or a mechanically disruptive event occurs that prevent the valve from being in a correct rotary position or moving to a different position, a method is provided to sense when the valve is in a particular position. The position sensing method utilizes a bar that can interrupt a photosensor beam at only one rotary position. When the photosensor beam is interrupted, this information feeds back to the programmable microcontroller which stops rotation precisely at that known position. The microcontroller can then automatically move the valve precisely to a new desired rotational position in a known rotational position relative to the "home" position at which it was stopped.

The apparatuses and devices of the invention optionally include a means to capture or divert undesired chemicals, poisonous chemicals or other contaminants in the test solutions to a storage container for subsequent safe disposal. By rotation of a rotary valve, the waste stream can be directed towards a storage container.

The apparatuses and devices of the invention optionally include Graphic User Interface (GUI) Software written in C# and Arduino software for inputting controller variables, changing automated timing of valves and pumps, calibrating sensors, monitoring and transmitting data collected by the fluorescence sensor, and recording valve positions, temperature, pH, and other device operation parameters.

Optionally, the apparatuses, devices and systems of the invention include a geographical position sensing (GPS) device. The GPS device allows for the identification of the geographic location at which the apparatus, device or system operates and/or collects data. In certain embodiments of the invention, the GPS device provides for the precise time and location of operation of one or more apparatuses, devices or systems. In other embodiments of the invention, the GPS device assists with the timing and location of other ballast monitoring operations, including the source of the water being measured.

The software and hardware of the devices, apparatuses and systems provided herein have been engineered to have effective user interfaces, as well as novel circuits and components, which reduce cost and improve performance for fluorescence detection. The devices, apparatuses and systems provided herein optionally comprises a novel type of computer-controlled valve control. Rotary stepper motors control the position of the handle on the manual valves in the devices, apparatuses and systems provided herein. Importantly, this type of valve positioning uses energy only when the valve is in motion.

The GSI website (http://www.nemw.org/gsi/index.htm), is incorporated herein by reference, and provides links to all GSI Standard Operating Procedures for tests.

The methods, systems and devices of the invention are designed for and provide compactness, ease of use, and ruggedness. All components can be housed in a rugged chassis, with clearly demarcated components to aid the operator, including clearly marked ballast water input tubes, output tubes for waste collection, power cords, and connectors for interfacing to a computer. Thus, the invention provides a device, system, or method as substantially described or illustrated herein.

The methods, systems and devices of the invention can be validated by comparison to standard ETV protocol measures (includes correlation, reproducibility, accuracy, positive and negative control behavior, etc.). The ETV protocols describe assays for assessing numbers of zooplankton, phytoplankton, and bacteria (*E. coli, Enterococcus, Vibrio cholera*, and heterotrophic plate count). These assays can be done on split samples to compare and correlate with results obtained with samples captured on the three mesh and filter sizes in the automated device, as well as the methods and systems of the invention.

To limit the discharge of pest species from ship ballast water, new and prospective regulations require sterilizing treatments or removal of live organisms from the ballast tanks before discharge. Current methods of verifying treatment efficacy are laborious and require human microscopic examination of large volumes of water. As an alternative for verifying the treatment, the devices, apparatuses, and systems of the invention provide a fully automated system that detects live microorganisms in the water in comparison to sterile water. The devices and apparatuses of the invention automatically sample and concentrate large volumes of water on reuseable filters, measure fluorescent metabolites produced by only live microorganisms, and employ fluid handling and electronic designs that are advantageous in that they are inexpensive, compact, and robust. The novel systems, apparatuses, devices and methods of the invention provide the same level of sensitivity at approximately 1/10th of the cost of current systems and methods. Fluorescein diacetate (FDA), a membrane permeable fluorogen, is used in the methods, systems, apparatuses, and devices of the invention to differentiate live from dead bacteria and algae.

In one embodiment, the systems of the invention pump the sample ballast water through a 0.2 micron filter to collect the organisms. The filter is then backwashed with BES buffer (pH 7) into a cuvette and mixed with an FDA stock solution injected by a syringe pump. The fluorescence is detected by an integrated fluorimeter, comprised of a low-noise photodiode, 472/525 nm excitation/emission filters, a low-bias current transimpedance amplifier with 108 gain, and a 16-bit analog to digital converter. The entire workflow is controlled through a graphical user interface implemented in C#. The interface acquires and analyses raw data, controls rotary and solenoid valves, and activates pumps to direct the sample and detection buffer. Self-calibration and feedback systems are incorporated to ensure precise control of water volumes and pressure and to monitor operation. Fluorescence data are collected at 1 sec intervals for periods up to 25 minutes. The apparatuses, devices and systems provided herein can be implemented from components that are low in cost, and can be housed in a compact chassis, such as one made by a 3D printer.

The systems, devices, apparatuses and methods have been successfully tested with environmental samples (Detroit River) and laboratory algae cultures, using deionized (sterile) water as a negative control. The environmental water and laboratory cultures were tested with and without a typical ballast treatment (chlorine) and other sterilizing techniques (heat). The limit of detection of the device is 100 nM fluorescein (the metabolite of FDA). Typically, Detroit River samples yield significant fluorescence within 5 minutes, signals show linearity with time and concentration of sample, and fluorescence is reduced to levels comparable to sterile water in response to heat or chlorine treatments of the sample.

Model organisms used to determine proper control over organism densities encompass several different types of organisms. For bacteria, a standard laboratory strain (K12) of *E. coli* can be used. However, *Enterococcus, Clostridium perfringens*, and *Vibrio cholera* can also be tested. The *Vibrio cholera* strain is may be a toxicogenic strain in which the toxin gene has been inactivated. For algae, *Myconastes, Chlorella*, and others can be used. For zooplankton, *Daphnia pulex* can be used.

Ambient water for testing of the methods, systems and devices of the invention can be collected from any natural source or any other aquatic source, including ballast water.

Provided in an embodiment is an automated device for detecting contaminants in a fluid, comprising a length of tubing that connects 3 or more chambers to a filter assembly and a detection apparatus, wherein the first chamber contains a fluid to be tested, a second chamber contains backwash fluid, a third chamber contains discarded fluid, and a fourth chamber contains a substrate; one or more valves, for controlling the flow of the fluid through the tubing; one or more pumps, for forcing the fluid through the tubing; and a vessel inside a detection apparatus. According to the device, the fluid to be tested is forced from the first chamber through the tubing by a first pump to the filter assembly, wherein the filter assembly contains a filter having two sides, an influent side and an effluent side, and a first valve is located along the tube at a location between the first pump and the influent side of the filter assembly; the filter assembly thereby concentrating the contaminants on the influent side of the filter in the filter assembly; the fluid is passed into the discarded fluid chamber; an amount of a backwash solution is forced from the second chamber through the tubing by a second pump to the filter assembly, and the backwash solution is passed through the filter on the effluent side of the filter, wherein the organisms concentrated on the influent side of the filter are forced from the filter and into the backwash solution, and a second valve is located along the tube at a location between the second pump and the effluent side of the filter assembly, the backwash solution then flows through the tubing and through the first valve into the vessel; an amount of the substrate is forced into the vessel; and any contaminants in the wash solution are detected by the detection apparatus.

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

Examples

I. Background

In our initial studies with manual ballast water valves, all valves were hand-operated, the solutions are moved by syringes, and fluorescence is read in a microplate reader. In studies with automated ballast water valves, the valves (Gems Sensors, B3317-520) and pumps (KNF Neuberger, PML3194NF-11) were computer controlled using a National Control Devices relay control board (ZADR810PROXR_USB). Fluorescence is automatically recorded on the same computer from an Ocean Optics fiber optics spectrometer (USB4000 FL CCD) with LED UV (380 nm) or blue (470 nm, peak excitation) light sources. Subsequent studies included the addition of an automatic solenoid-driven injector for the introduction of FDA into the cuvette.

Figure 3:
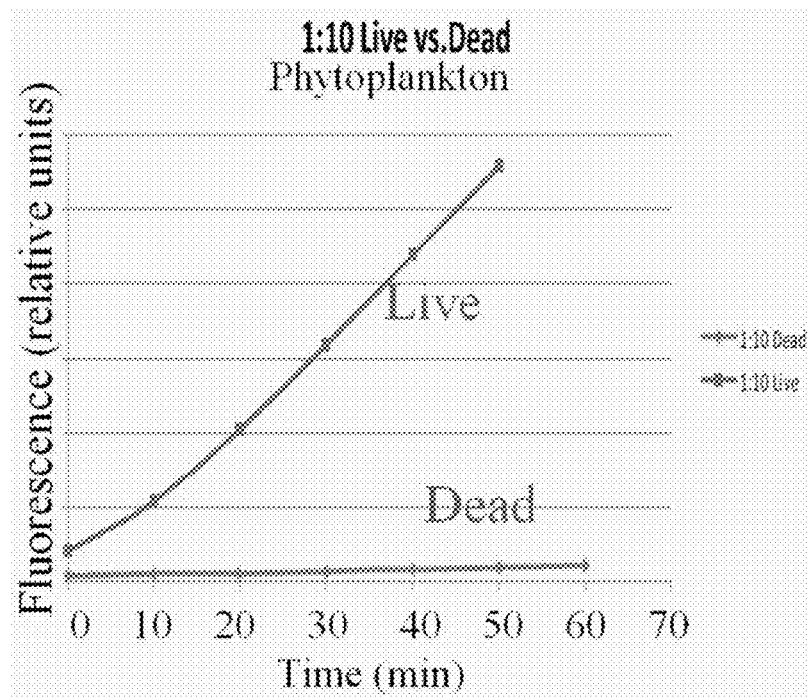
FIG. 3 illustrates the increase in FDA-containing media fluorescence in presence of live algae (*Myconastes*), compared to dead (heat-killed) algae (in Jaworski's media, buffered to pH 7.0).
Figure 4:
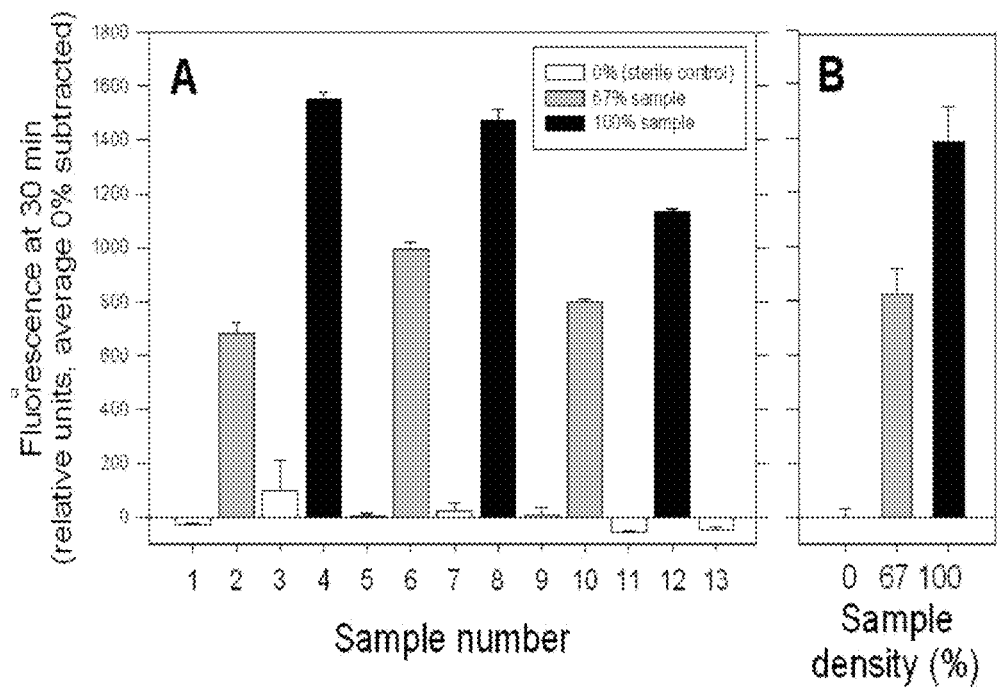
FIG. 4 illustrates Detroit River (DR) sample analyzed repeatedly on same filter. (A) Successive applications of control (sterile, denoted by clear bars), 67% dilution (denoted by gray shading) and full strength (100%, denoted by black shading) DR water, analyzed with the same filter, and back-washed with sterile water between each measurement. (B) Average responses of the 7 control and 3 DR measurements at each density.
Figure 5:
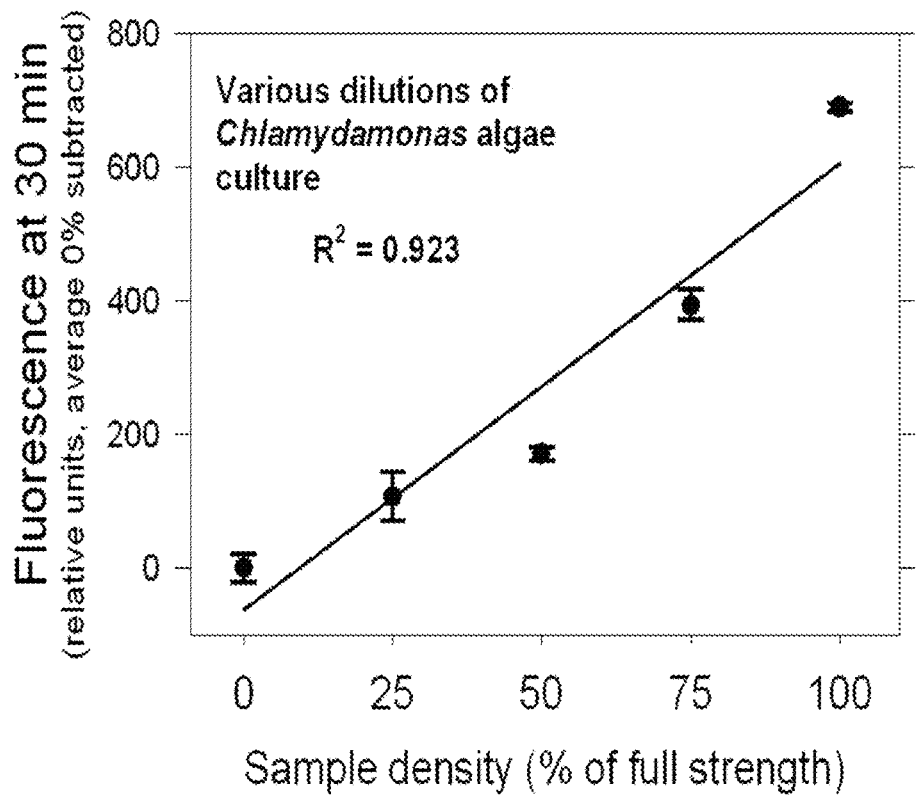
FIG. 5 illustrates fluorescence responses with various dilutions of *Chlamydamonas* algae culture. Linearity of response is indicated by R2=0.923. Points and error bars represent triplicate means+sem.
Figure 6:
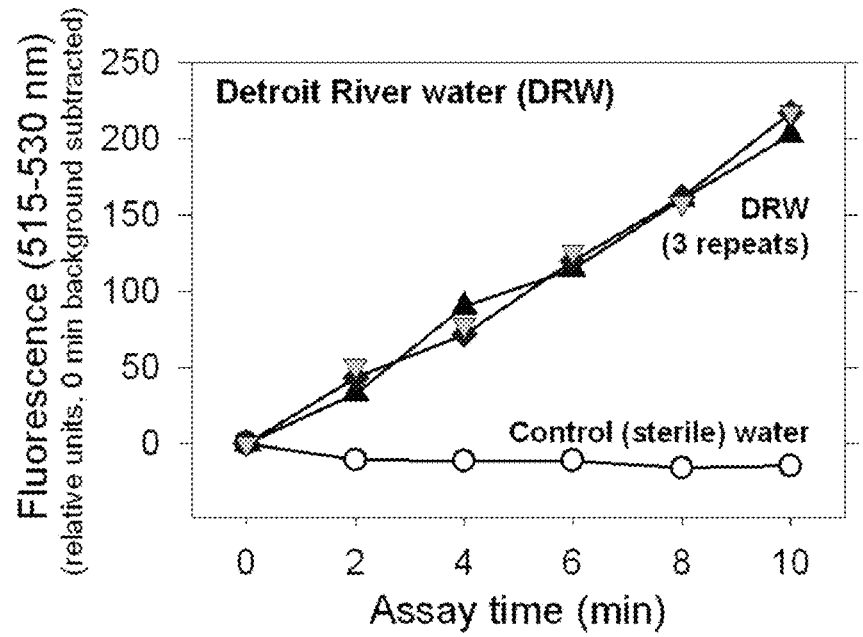
FIG. 6 illustrates Detroit River water assayed in triplicate by semi-automated device (automated sample loading and filter backwash; manual FDA injection). Note also the rapid (10 min) analysis.

Several basic functions of the device are illustrated in the figures provided herein. FIGS. 2 and 3 illustrate the results differentiate live from dead organisms. FIG. 4: the filters are washable and reusable; FIGS. 4 and 5 the response is proportional to the amount of live organisms; and FIG. 6: results are rapid and reproducible.

The devices, systems and methods of the invention can be tested with at least 3 kill methods similar to BWTs: hypochlorite (bleach applied to achieve 10 ppm total residual chlorine for 19 hours, as required by the Michigan General Permit (MIDEQ, 2006)), ultraviolet light (>200,000 microwatts-sec/cm$^2$, (MIDEQ, 2006)), and NaOH (pH to 12 for 24 hr, followed by neutralization. Additionally, live-dead comparisons for organisms killed by heat (autoclaving or 95° C. for 15-30 min) have been tested, with results anticipated as similar to a proposed microwave-based heat BWT (Boldor et al., 2008). Data are provided for the heat and hypochlorite kill methods (FIGS. 12 and 13, respectively).

II. Heat Kill Example

Figure 12:
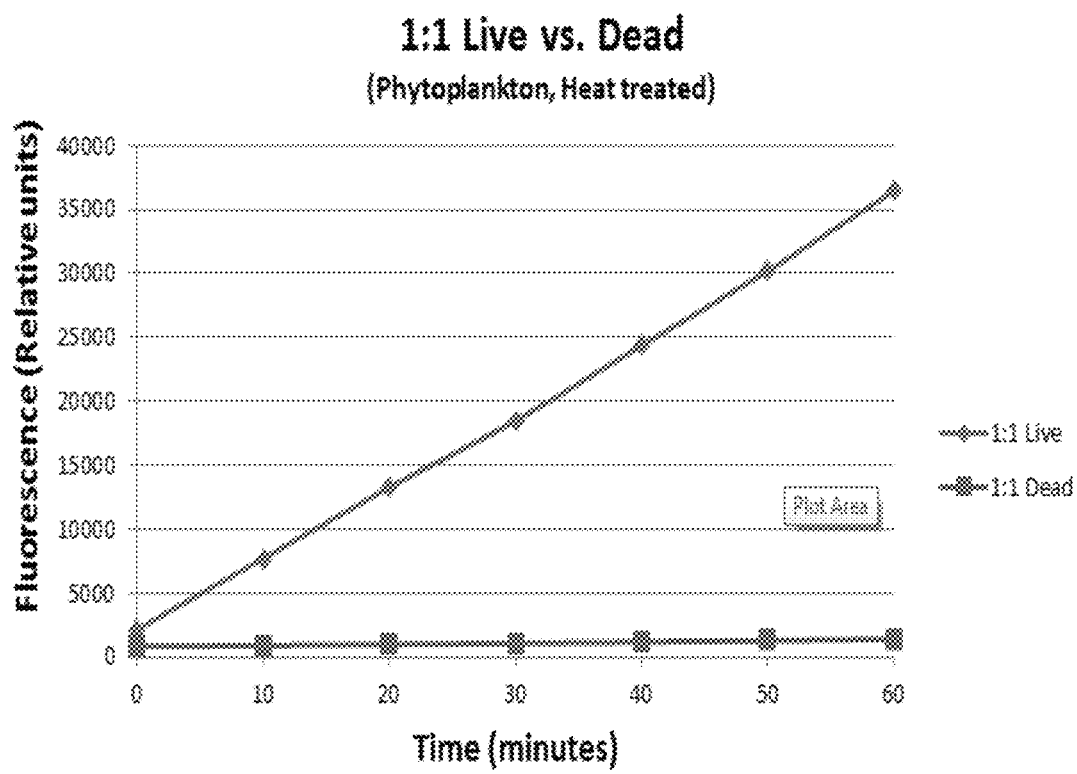
FIG. 12 illustrates the linearity of the increase in fluorescence over time, and the dependence of fluorescence production on live organisms. Fluorescence response with *Myconastes* algae culture; top line: live culture; bottom line: heat-killed (92 deg. C., 30 min) culture.
Figure 13:
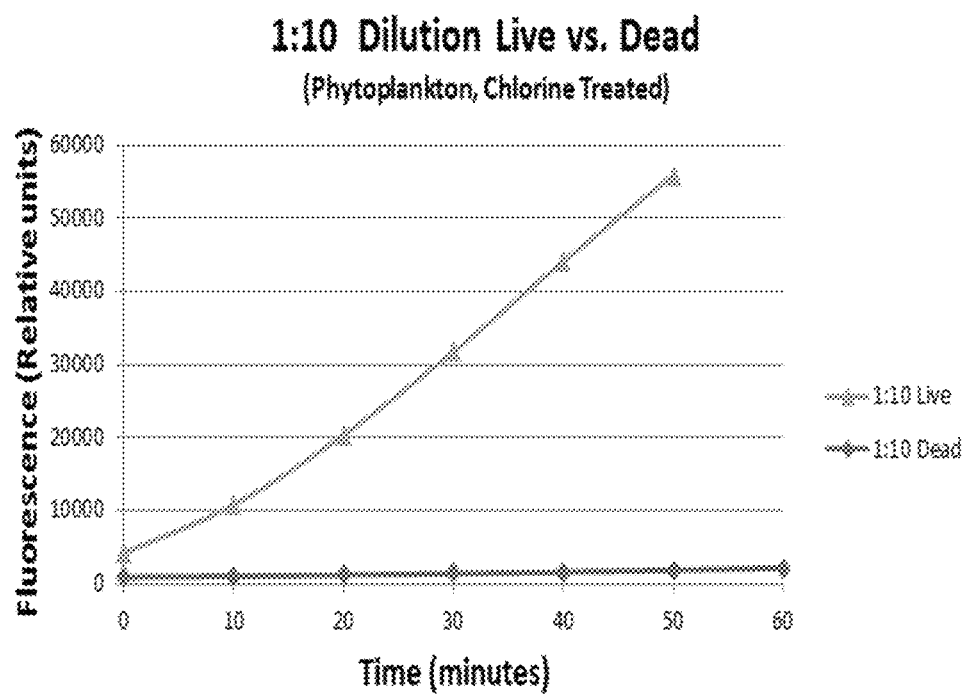
FIG. 13 illustrates the linearity of the increase in fluorescence over time, and the dependence of fluorescence production on live organisms. Fluorescence response with *Myconastes* algae culture; top line: live culture; bottom line: chlorine-killed (24 hr., 3 mg/L) culture.

FIG. 12 illustrates data obtained from a heat-kill experiment. Linear fluorescein diacetate (FDA)-hydrolysis activity by live algae culture and reduction of FDA-hydrolysis activity of algae culture killed with heat. *Myconastes* algae culture was grown in Jaworski's medium (http://www.ccap.ac.uk/media/recipes/JM.htm). 2 mL aliquots of culture were either held at room temperature or were placed in a 92° C. heating block for 30 minutes, filtered onto 0.2 μm cellulose acetate filters, backwashed with 0.5 mL JB, and then triplicate 150 μL aliquots of each backwash were transferred in triplicate to a black 96-well plate. FDA was added as PBFDA, a phosphate buffered (pH 7) solution containing 20 μg FDA/mL was then added and the fluorescence was read in a fluorometric plate reader in relative fluorescence units. From this experiment and others like it, it was determined that the production of fluorescein, a fluorescent derivative of FDA, from FDA by live cells is linear in time and that killing cells with heat blocks this reaction.

III. Chlorine-Kill Example

FIG. 13 illustrates data obtained from a chlorine-kill experiment. Linear FDA-hydrolysis activity by live algae culture and reduction of FDA-hydrolysis activity of algae culture killed with chlorine (hypochlorite). An aliquot of *Myconastes* algae culture, grown in Jaworski's medium (http://www.ccap.ac.uk/media/recipes/JM.htm) was treated with hypochlorite solution (bleach) at a concentration of 3 mg hypochlorite/L. Both treated and untreated cultures were incubated for 24 hours at room temperature (~22° C.). Next, 10 mL of each culture was diluted 10-fold to 100 mL; each was filtered through an 0.2 μm cellulose acetate filter; 1 mL Jaworski's buffer (JB, same salts as Jaworski's medium without the nutrients, and adjusted to pH 7) was then used to backwash the filter into a disposable centrifuge tube from which 3 150 µL aliquots were pipetted onto a black 96-well plate. The assay was started by addition of 150 µL JBFDA solution (JB solution containing 20 µg FDA/mL, yielding a final assay concentration of 10 µg FDA/mL). Fluorescence was recorded on a fluorimetric plate reader in relative fluorescence units. As in the previous experiment, the production of fluorescein from FDA by live cells is linear in time, and cells killed with chlorine also do not produce this reaction. Chlorine treatment is a frequently used ballast water treatment. Hence, this assay may be useful in assessing the efficacy of chlorine treatments.

IV. Analysis of Detroit River Water

Figure 14:
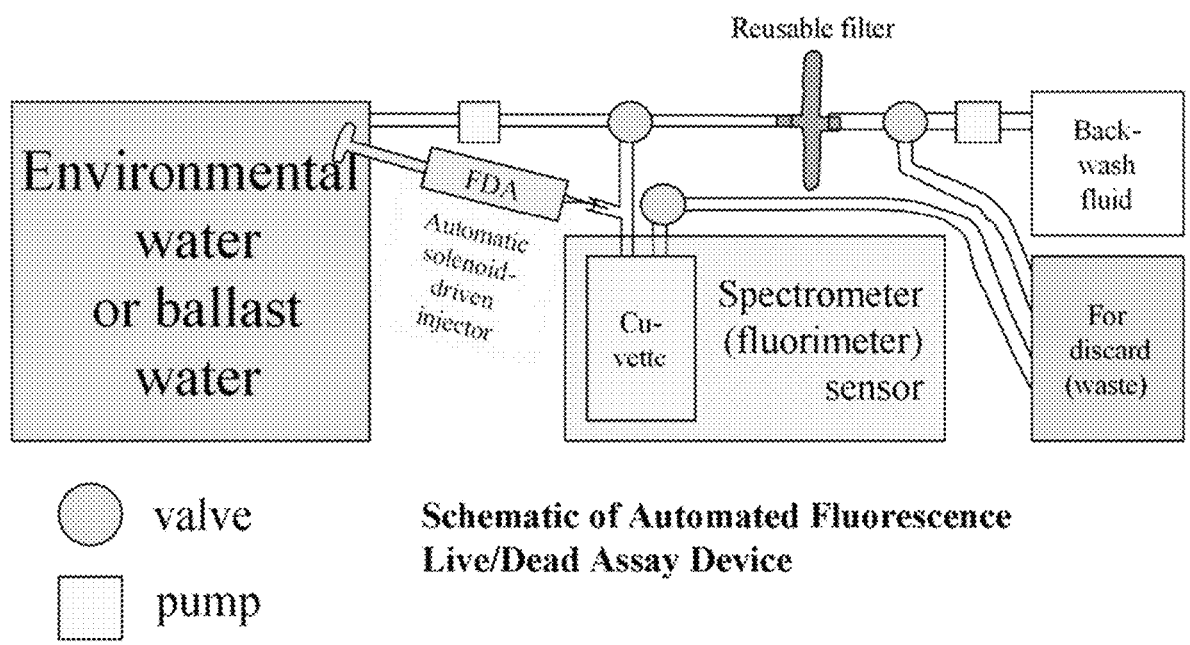
FIG. 14 provides a schematic of automated fluorescence live/dead assay device. Pumps (squares) are KNF Neuberger, PML3194NF-11; valves (circles) are Gems Sensors, B3317-520; automatic solenoid-driven injector (needle).
Figures 15A, 15B:
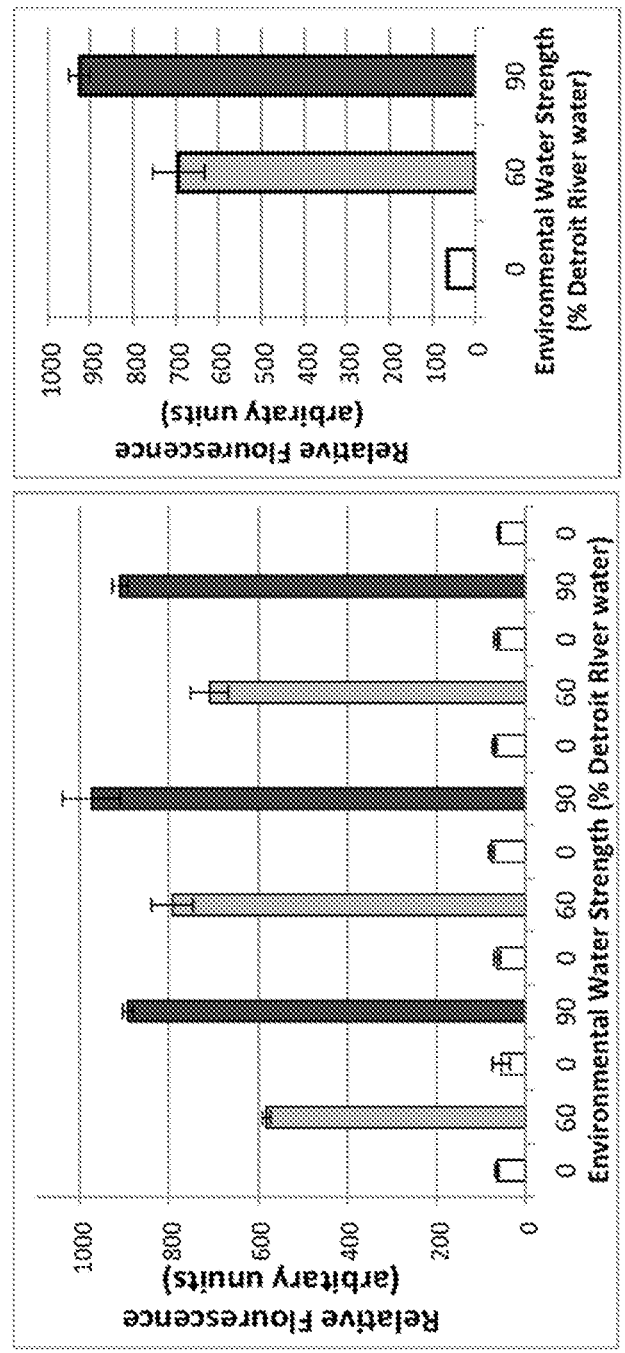
FIG. 15 illustrates the results of testing Detroit River Water samples. (A) Triplicate assays of deionized water (DI, clear bar), 60% (lightly colored bar), and 90% Detroit River water (dark bar), mean±sem. (B) Summary averages of the 7 DI, 3 60%, and 3 90% samples shown at the left. Correlation of sample strength v. fluorescence intensity gave an $R^2$ of 0.982. The experiment was done manually.

FIG. 14 provides a schematic of automated fluorescence live/dead assay device. FIG. 15 illustrates the results of analyzing Detroit River Water samples. The experiments were carried out as follows. Multiple FDA assays of environmental water with backwash and re-use of the same filter. Detroit River water was collected near Belle Isle beach on Belle Isle, Detroit, and diluted to 90% full strength and 60% full strength with sterile deionized water (DI). For each assay, 100 mL of water (either a DI control, or 60% or 90% Detroit water) was pushed through a 0.2 µL cellulose acetate filter. The filter was then backwashed with 3 mL of JB. 150 µL of the backwash fluid (which contains the organisms that had been captured on the filter) was then put, in triplicate, in a black 96-well plate, 150 µL of JBFDA was added to each well, and the fluorescence was recorded for 60 min on a fluorimetric plate reader. The filter was further backwashed for cleaning with 100 mL of DI, and this cleaning backwash fluid was discarded. The next sample was then pushed through the same filter and the process was repeated. The first thirteen wash/backwash/clean cycles are shown. The filter performed similarly up to 24 cycles before failing. In this experiment, the Detroit River samples alternated with the DI controls in order to determine if the cleaning backwash decreased the background to initial levels. The left graph of FIG. 15 shows the mean±sem of the triplicate assays of DI (clear bars), 60% (lightly colored bars), and 90% Detroit River water (dark bars) in relative fluorescence units for each sample at the 30 min time point after addition of the JBFDA. The right graph of FIG. 15 summarizes the averages of the 7 DI, 3 60%, and 3 90% samples shown at the left. Correlation of sample strength v. fluorescence intensity gave an $R^2$ of 0.982.

Discussion: The results of the experiment show (a) that the control levels of FDA hydrolysis stayed low, comparable to the first control that was tested before any Detroit River water had been put on the filter; (b) that Detroit River water had enough live organisms to cause measureable FDA hydrolysis; (c) that the amount of fluorescence increases with the number of organisms as reflected by the correlation of the dilution of environmental samples with the signal produced; and (d) that 0.2 µm cellulose acetate filters can be re-used multiple times.

V. Automated Assay Examples Using Detroit River Water

Figure 16:
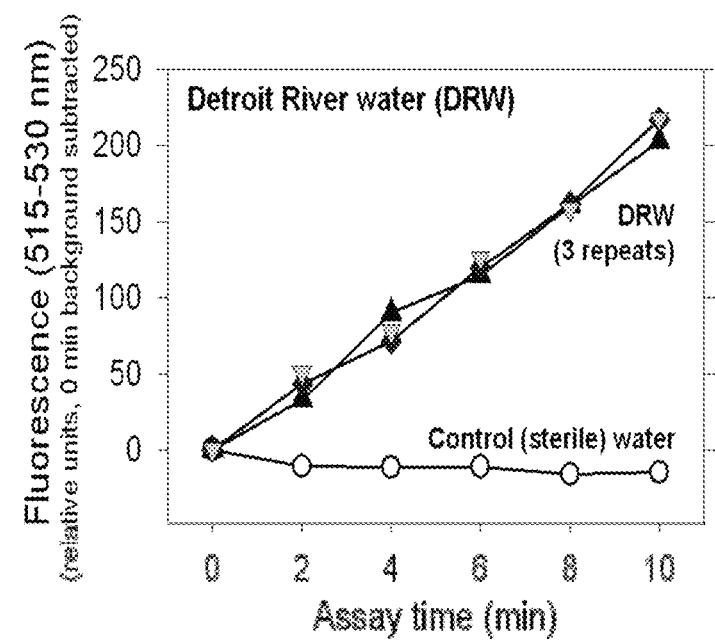
FIG. 16 illustrates the results of automated assays of Detroit River Water samples. Three replicates of samples of the same Detroit River water samples were alternately assayed with sterile water samples by automated FDA analysis device. The last 3 assays were monitored and analyzed remotely, using TeamViewer software.
Figure 16:
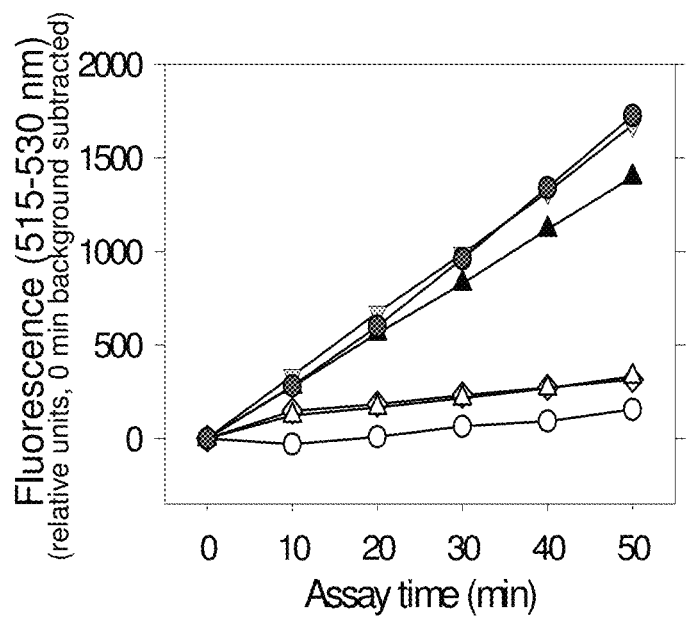

FIG. 16 illustrates the results of automated assays of Detroit River Water samples. The experiments were carried out as follows. FDA assays of Detroit River water run on the prototype automated device illustrated schematically by FIG. 14. For both (A) and (B), Detroit River water (DRW) was collected near Belle Isle beach on Belle Isle, Detroit. The prototype device pumped 100 mL of the sample (either DRW or a DI sterile water control through a 0.2 µm cellulose acetate filter (labeled as "reusable filter" in the schematic). Next, approximately 3 mL of JB backwash fluid was pumped in the reverse direction through the filter, while the valve above the cuvette was changed so the fluid was directed into the cuvette. Simultaneously, 10 µL of a concentrated FDA stock solution (2 mg FDA/mL acetone) was injected by an automated syringe into the backwash fluid filling the cuvette. Fluorescence in the cuvette in the range of 515-530 nm was measured with a 470 nm LED excitation light source and an Ocean Optics spectrometer. FIG. 16(A): Four automated assays were conducted, in the following order: DI, DRW, DRW, DRW. The backwash volume was 3 mL; the filter was changed after each test. FIG. 16(B): Fully automated assay, with re-use of the same filter. The backwash volume for sample measurement was 3.4 mL. After measuring fluorescence for 50 min, the filter and cuvette were backwashed for cleaning with 100 mL DI, followed by the next sample to be tested being pumped through the cleaned 0.2 µm filter. Six automated assays were conducted; the last 3 assays were monitored and analyzed remotely, using TeamViewer software.

Discussion: From these data, we conclude that with the automated system, (a) environmental samples can show significant results (i.e., different from sterile water controls) within 10 min, (b) as with fluormetric plate reader assays, the production of fluorescence in the presence of live organisms is linear with time, (c) assays can use samples backwashed off of 0.2 µm filters, (d) the automated system can wash the filters with a DI backwash, to yield reproducible data in serial re-tests of the same samples, and (e) the entire system can be remotely monitored and controlled with internet based computer control software (Team Viewer).

VI. Semi-Automated Assay Examples Using Detroit River Water

Figure 17:
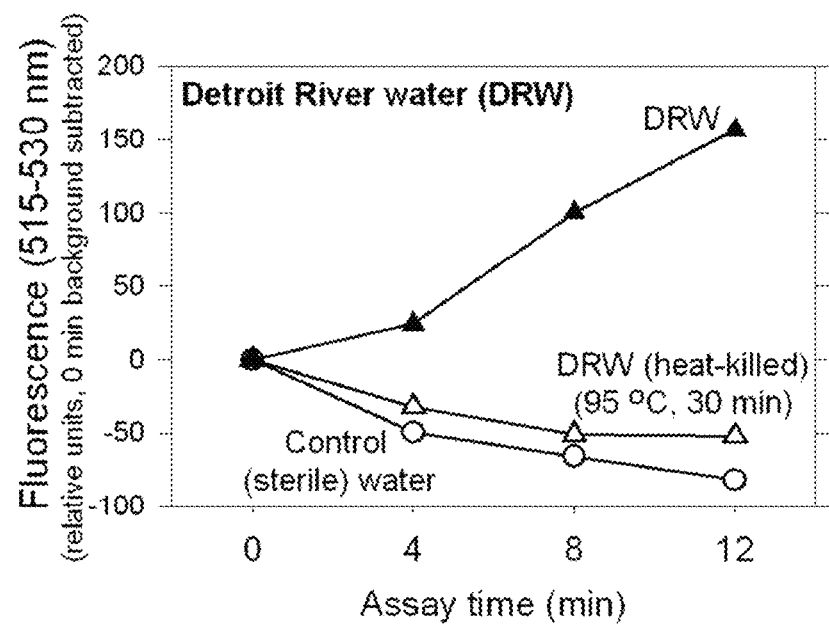
FIG. 17 illustrates semi-automated assays of Detroit River Water. Sample filtering and backwash was automated. Transfer to cuvette and injection of stock FDA solution was manual. Assays show significant results within 12 min Heat killed environmental samples (95 C, 30 min) also showed a significantly decreased FDA breakdown signal compared to experimental sample.

FIG. 17 illustrates data from semi-automated assays showing the effect of heat-killing organisms in Detroit River Water (DRW). The experiments were carried out as follows. Sample filtering and backwash were automated. Transfer to cuvette and injection of stock FDA solution was manual. Detroit River water (DRW) was collected near Belle Isle beach on Belle Isle, Detroit. The prototype device pumped 100 mL of the sample (either DRW or a DI sterile water control through a 0.2 µm cellulose acetate filter (labeled as "reusable filter" in FIG. 14). Next, approximately 3 mL of JB backwash fluid was pumped in the reverse direction through the filter, and the backwashed fluid was collected for subsequent assay. 2.5 mL of the backwash fluid was pipetted into the cuvette and then 0.5 mL of JBFDA was added to the cuvette for assay (the concentration of FDA in the JBFDA was adjusted to be equivalent to 10 µL of 2 mg/mL FDA in acetone in the final solution). Fluorescence in the cuvette in the range of 515-530 nm was measured with a 470 nm LED excitation light source and an Ocean Optics spectrometer. Samples were measured in the following order: DI, DRW, heat-treated DRW (heat treatment was 95° C., 30 min on a heating block prior to assay).

Discussion: The results show (a) significant differences of DRW from sterile control and heat-treated DRW within 12 min; and (b) heat-treatment of DRW samples did not differ significantly from the sterile control.

VII. Shipboard Testing Example

Figures 18, 19:
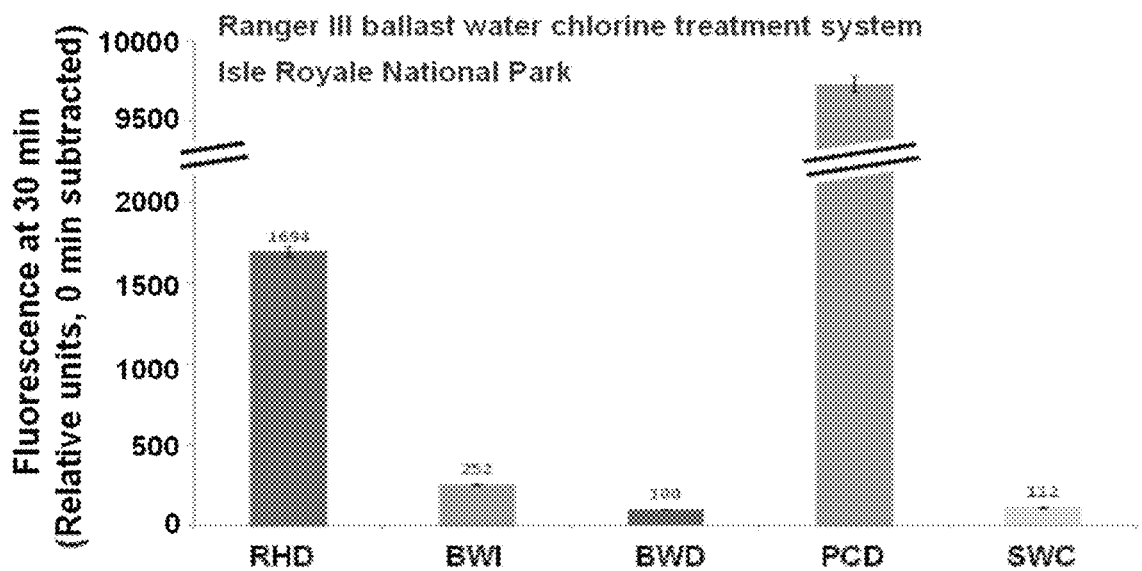
FIG. 18 illustrates the results of shipboard testing using a manual FDA assay, with a fluorescent plate reader. Vessel: National Park Service ship Ranger III, using a chlorine-based ballast water treatment system.
FIG. 19 provides a chart of the most probable number (MPN) of coliforms and *E. coli* coliforms found in five water samples, as measured by Quanti-Tray. Rock Harbor Direct (RHD), Ballast Water Intake (BWI), Ballast Water Discharge (BWD), Portage Canal Direct (PCD), and Sterile Water Control (SWC).

FIG. 18 illustrates the results of shipboard testing using a manual FDA assay, with a fluorescent plate reader, and FIG.

19 provides a chart of the most probable number (MPN) of coliforms and *E. coli* coliforms found in five water samples, as measured by Quanti-Tray. The experiments were carried out as follows. FDA assay of environmental and ballast water samples from the Ranger III, the passenger/cargo ship of the Isle Royale National Park. Water samples were RHD, collected directly from Rock Harbor (Isle Royale); BWI, collected inside the ship from the ballast water intake (water pumped in from Lake Superior as the ship began its trip to Houghton) just before the water entered the ballast tank; BWD, collected during ballast tank discharge, after 3 hours chlorine treatment (3 mg hypochlorite from bleach/L) and neutralization by ascorbic acid; PCD, collected directly from the Portage Canal at Houghton; SWC, a sterile water control that was processed similarly to the environmental and ballast tank samples. Water samples were stored refrigerated or on ice during a one day return trip to Detroit, after which they were assayed for FDA hydrolysis activity and *E. coli*/coliform counts using IDEXX Quantitray-2000 and Colilert-18. FIG. 18: To measure FDA hydrolysis activity, 100 mL of the sample was filtered on a 0.2 μm cellulose acetate filter, backwashed with 1 mL of JB, and then triplicate 150 μL aliquots of the backwash fluid were pipetted into a black 96-well plate and the FDA hydrolysis measurement was initiated by addition of 150 μL JBFDA. Fluorescence was read in a fluorometric plate reader. Bars represent mean±sem of the triplicate measurements at 30 min, with the 0 min background subtracted. FIG. 19: Results of measurements of coliforms and *E. coli* using Colilert in Quantitray-2000.

Discussion: We conclude from this experiment (a) that the FDA method has the sensitivity to make such measurements from environmental and ballast water samples, (b) that FDA measured a reduction of the amount of live organisms after treatment with chlorine, (c) that the ports where discharge of ballast water could potentially cause harm already have high numbers of live organisms, and (d) that the levels of microorganisms at these ports are low compared to prospective ballast water regulations by the IMO. For example, even the Portage Canal Direct sample has only 2 MPN.

VIII. Instant Ocean Example

Systems with organisms that have been treated with Instant Ocean (simulated ballast water exchange) can be tested. These experiments can ascertain that the after effects of the above-provided kill methods do not cause false positive or false negative signals. It should be noted that none of the chemicals used in the above treatments are present during the fluorogenic assay itself, as the filter-backwash system changes the medium in which the organisms are measured. Other treatment methods, such as ozone, hydrogen peroxide, and menadione (*SeaKleen* (Wright et al., 2009)) are also possible.

IX. Field Test Example

Figure 23:
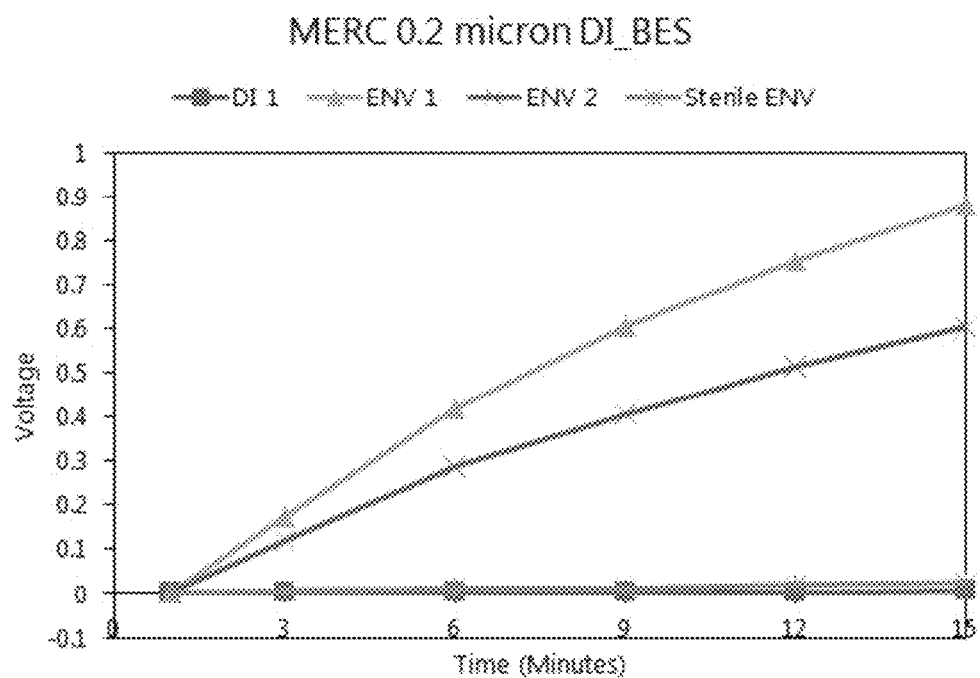
FIG. 23 is a graph depicting the response for organisms captured on 0.2 micron filters.

Applicants' ballast water verification system was tested under field conditions.
A brief summary of the results obtained is provided below.
The ambient intake samples produced measureable "live" signals within 5 min (FIG. 23) from organisms captured on both 0.2 μm filters and on 10 μm nylon mesh. Replicate measurements were in good but not identical agreement with one another (e.g., ENV1 and ENV2 in FIG. 24). The responses for organisms captured on 0.2 μm filters were larger than for organisms captured on 10 μm nylon mesh (FIGS. 23, 24), after 15 min, the signal for organisms captured on 10 μm is less than 10% of the signal on 0.2 μm. One liter samples filtered on 10 μm mesh produced larger signals than the standard 100 ml samples.

Figure 24:
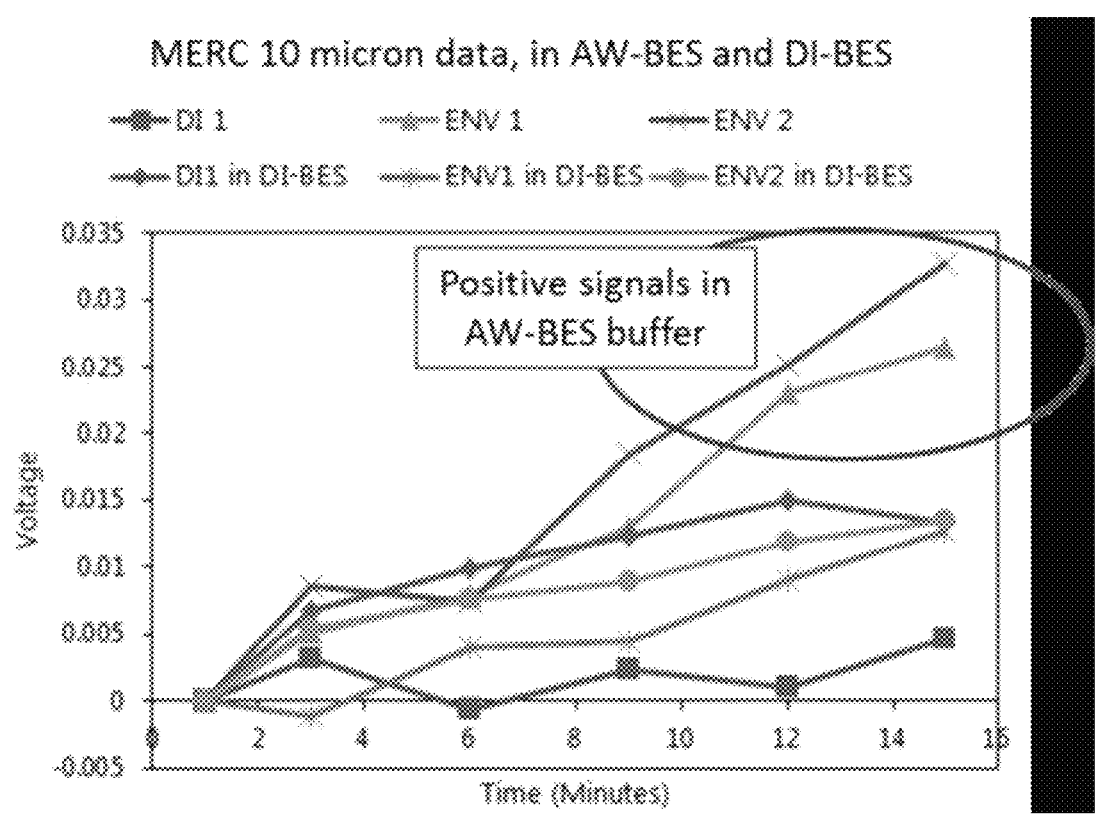
FIG. 24 is a graph depicting the results of assays conducted with sterile ambient BES buffered media and BES buffered water, using a 10 Micron mesh filter.
Figure 25:
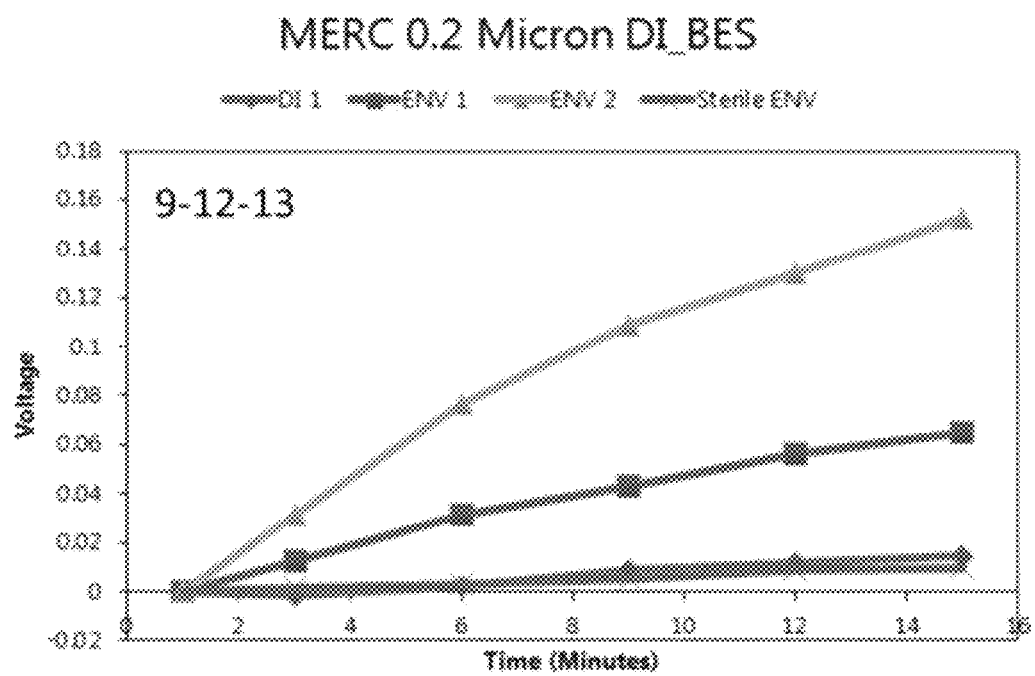
FIG. 25 is a graph depicting the response for live organisms captured on 0.2 micron filters after 3 days hold in ballast tanks.

Assays conducted with sterile ambient BES buffered media gave a higher signal in some cases than assays conducted with BES buffered water (i.e., with lower than ambient salinity; also shown in graph in FIG. 24). Live signals measured after 3 days hold in ballast tanks were lower than for intake water (FIG. 25) (note the lower voltages obtained on 9-12-13). For 7 days hold in ballast tanks, the signals were even lower. The flexibility of the system was demonstrated, as the field test facility had Wi-Fi internet, which enabled scientists to remotely control and monitor the experiments.

The capture/backwash system worked perfectly, having no significant changes of flow rate or failure, for 8 cycles for the 0.2 μm filter and for 6 cycles of the 10 μm mesh (the total number of cycles). All equipment, chemistry, and methods were robust.

X. Additional Examples

Biological and chemical experiments: Tests of BES (N,N-Bis(2-hydroxyethyl)-2-aminoethanesulfonate as the FDA incubation buffer were performed, compared buffering deionized water and sterile-filtered ambient water as the buffer.

Figure 20:
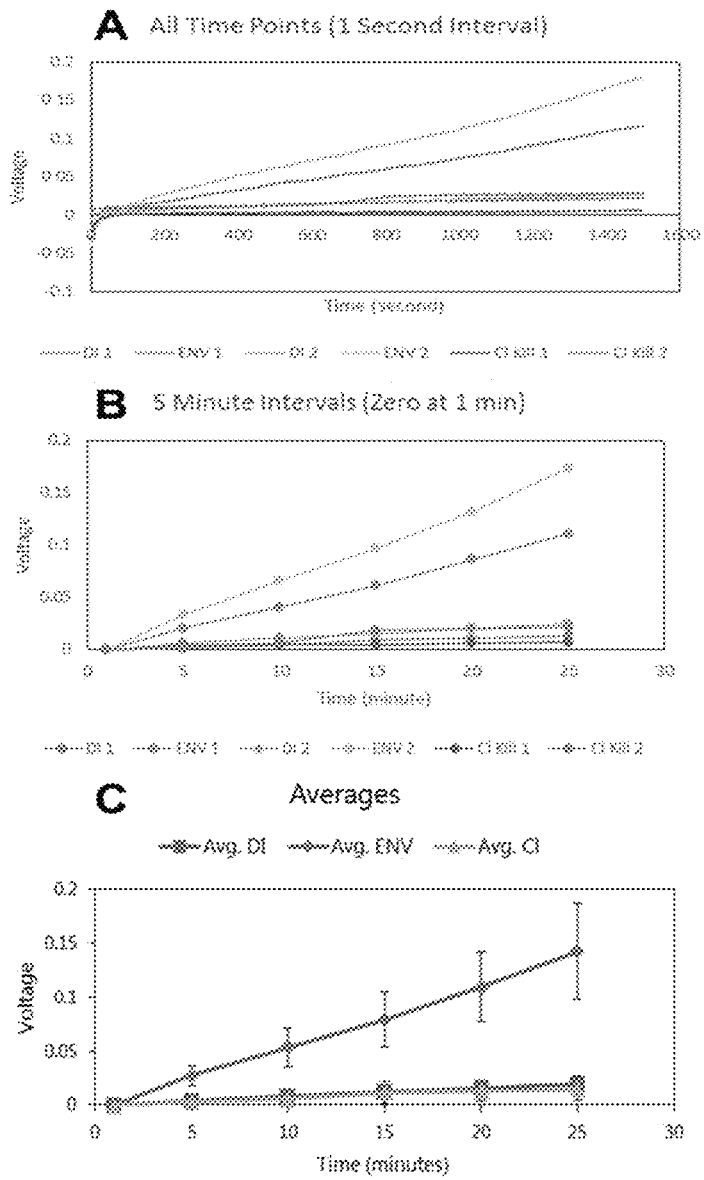
FIG. 20 (A) illustrates the high signal to noise level of the new electronic sensor circuits (the graph illustrates data logged at 1 sec intervals for all samples [DI1 and DI2, sterile water samples; ENV1 and ENV2, DR samples not treated with Clorox; Cl Kill1 and Cl Kill 2, Clorox-treated]; (B) illustrates data from FIG. 20(A) adjusted for analysis (each curve is "zeroed" at the one minute time-point. Points at 5-minute intervals are time-averaged data from 11 seconds of time-points): (C) illustrates averages of the replicate experimental tests illustrated in FIGS. 20 (A) and (B) (the Chlorine-treated environmental water result is practically identical to the sterile water results and is much lower than the untreated environmental water measurements).

Chlorine treatment tests were performed. Using the automated system, several chlorine-treatment experiments (Detroit River [DR]environmental water treated with 10 mg/L sodium hypochlorite [Clorox bleach], neutralized with ascorbic acid after 24 hr, compared to DR without treatment held same amount of time) were done. Data from a representative experiment is illustrated at FIG. 20, which provides an illustration of data quality, system performance, and analysis. The three parts of FIG. 20(A) illustrates the high signal to noise level of the new electronic sensor circuits (the graph illustrates data logged at 1 sec intervals for all samples [DI1 and DI2, sterile water samples; ENV1 and ENV2, DR samples not treated with Clorox; Cl Kill1 and Cl Kill 2, Clorox-treated]. There is a "settling in" period of about 1 min until the FDA hydrolysis rate stabilizes after which the activity is almost linear for a minimum of 25 min. The slope of each curve is the rate of FDA hydrolysis (fluorescence detected)). FIG. 20(B) illustrates data from FIG. 20(A) adjusted for analysis (each curve is "zeroed" at the one minute time-point. Points at 5-minute intervals are time-averaged data from 11 seconds of time-points). FIG. 20 (C) illustrates averages of the replicate experimental tests illustrated in FIGS. 20 (A) and (B) (the Chlorine-treated environmental water result is practically identical to the sterile water results and is much lower than the untreated environmental water measurements).

Figure 21:
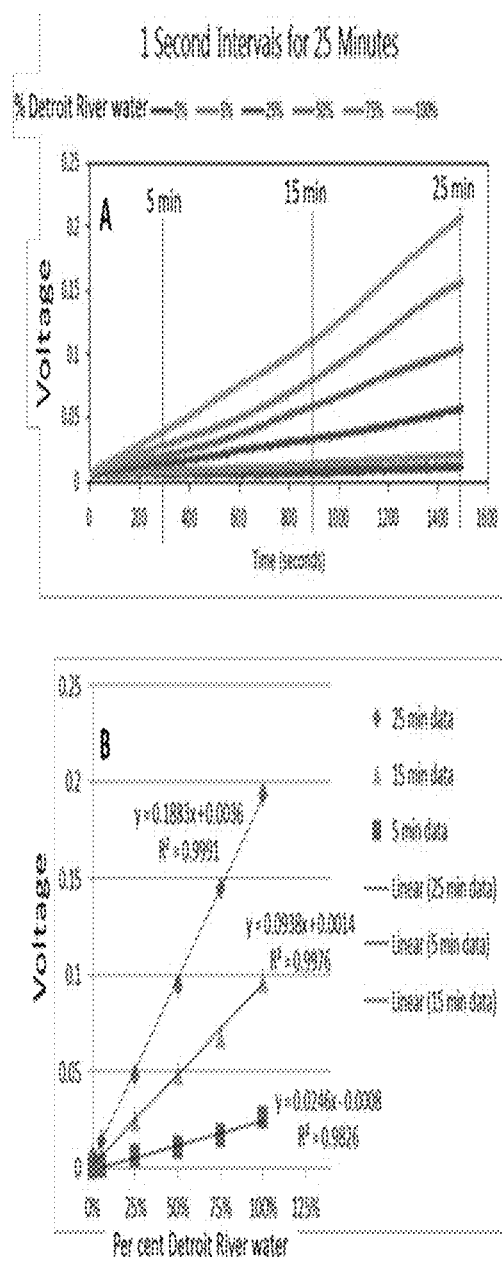
FIG. 21. (A) Dilutions of Detroit River environmental samples were tested. The graph illustrates the excellent signal to noise ratio and the linearity with time; (B) illustrates the linear relationship of the fluorescence signal with % dilution is analyzed. The $R^2$ values indicate that the linearity of the relationship is almost as good for the much smaller signal recorded at 5 min incubation ($R^2$=0.983) as for 25 min incubation ($R^2$=0.999).
Figure 22:
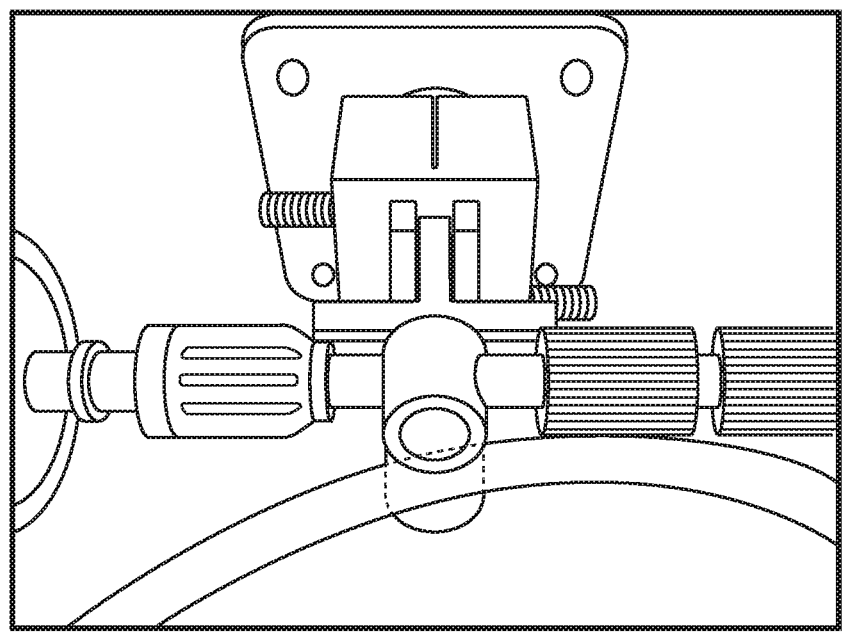
FIG. 22 is a photograph of a clamp on the handle of a valve in certain embodiments of the system, device and apparatuses of the invention. Applicants' devices, systems and apparatuses that use the rotary stepper motor for controlling the position of the hand on the manual valves consume less energy while operating.

Proportionality to amount of sample when run with the fully automated system. Data illustrated in FIG. 21(A) show excellent signal to noise and linearity with time. Various dilutions of a Detroit River environmental sample (0%, 5%, 25%, 50%, 75%, and 100%) were tested. FIG. 21 (B) illustrates the linear relationship of the fluorescence signal with % dilution is analyzed. The $R^2$ values indicate that the linearity of the relationship is almost as good for the much smaller signal recorded at 5 min incubation ($R^2$=0.983) as for 25 min incubation ($R^2$=0.999).

Various types of biological samples were tested, including laboratory grown algae, environmental samples from various locations, and bacteria. Tests of various filters (0.2 μm) and mesh sizes (10 μm) were also performed. Improved filter function for 0.2 μm filter function was obtained with the 0.22 μm 33 mm PES filter (Millipore, USA). We have obtained >45 reuses of the same filter of this type, with only slight diminution of flow through it.

The automated device for measuring *E. coli*, as described by Nijak et al. (2012; ENVIRONMENTAL ENGINEERING SCIENCE Volume: 29, Issue: 1, pages: 64-69; DOI: 10.1089/ees.2011.0148), is hereby incorporated by reference.

CITATIONS

Adam G, Duncan H, Development of a sensitive and rapid method for the measurement of total microbial activity using fluorescein diacetate (FDA) in a range of soils. Soil Biology & Biochemistry, 33 (2001) 943-951.

Balagadde F K, You L, Hansen C L, Arnold F H, Quake S R, Long-term monitoring of bacteria undergoing programmed population control in a microchemostat. Science, 309 (2005) 137-140.

Boldor D, Balasubramanian S, Purohit S, Rusch K A, Design and implementation of a continuous microwave heating system for ballast water treatment. Environmental Science & Technology, 42 (2008) 4121-4127.

Bronte C R, Evrard L M, Brown W P, Mayo K R, Edwards A J, Fish community changes in the St. Louis River estuary, Lake Superior, 1989-1996: Is it ruffe or population dynamics? Journal of Great Lakes Research, 24 (1998) 309-318.

Clavero M, Garcia-Berthou E, Invasive species are a leading cause of animal extinctions. Trends in Ecology & Evolution, 20 (2005) 110-110.

Geary J R, In-situ optical sensing for the detection and quantification of pathogen indicator organisms. Ph.D. Notre Dame, Notre Dame, Ind. 2009, 233 pp.

Kelly D W, Vectors and pathways for nonindiginous aquatic species in the Great Lakes. Transportation Research Board Special Report 291, http://onlinepubs.trb.org/onlinepubs/sr/sr291_kelly2.pdf (2007) 27 pp.

MIDEQ, Ballast Water Control General Permit: Port Operations and Ballast Water Discharge. State of Michigan Department of Environmental Quality, Permit No. MIG140000 (2006) 23 pages.

Minnesota, Draft ballast water discharge certification to EPA certifying compliance with section 401 Clean Water Act. To: Tinka G Hyde, USEPA (2012) May 7, 2012.

Nijak G M, Geary J R, Larson S L, Talley J W, Autonomous, wireless in-situ sensor (AWISS) for rapid warning of *Escherichia coli* outbreaks in recreational and source waters. Environmental Engineering Science, 29 (2012) 64-69.

NSF International, Generic Protocol for the Verification of Ballast Water Treatment Technology. http://nepis.epa.gov/Exe/ZyPURL.cgi?Dockey=P10097A4.txt, Produced for the U.S. Environmental Protection Agency Environmental Technology Verification Program, in cooperation with U.S. Coast Guard and the U.S. Naval Research Laboratory (2010) 156 pp.

Pothoven S A, Vanderploeg H A, Warner D M, Schaeffer J S, Ludsin S A, Claramunt R M, Nalepa T F, Influences on *Bythotrephes longimanus* life-history characteristics in the Great Lakes. Journal of Great Lakes Research, 38 (2012) 134-141.

Ram J L, Device for collection and preservation of tissue or stool samples. World Intellectual Property Organization, International Publication Number WO 2009/038763 A1 (2009) 20 pp.

Ram J L, Ram M L, Baidoun F, Authentication of canned tuna and bonito by sequence and restriction site analysis of polymerase chain reaction (PCR) reaction products of mitochondrial DNA. Journal of Agricultural and Food Chemistry, 44 (1996) 2460-2467.

Ram J L, Ritchie R P, Fang J, Gonzales F, Selegean J P, Sequence-based source tracking of *Escherichia coli* based on genetic diversity of beta-glucuronidase. Journal of Environmental Quality, 33 (2004) 1024-1033.

Ram J L, Thompson B, Turner C, Nechvatal J M, Sheehan H, Bobrin J, Identification of pets and raccoons as sources of bacterial contamination of urban storm sewers using a sequence-based bacterial source tracking method. Water Research, 41 (2007) 3605-3614.

Savino J, Kostich M, 2000. Round Goby: An Exotic Fish in the Great Lakes. GLSC Fact Sheet 2000-1 (http://www.glsc.usgs.gov/_files/factsheets/2000-1%20Round%20Goby.pdf). Great Lakes Science Center, Ann Arbor.

Schrock M, Riffle C, Dindal A, McKernan J, Enriquez J, Mycometer-test rapid fungi detection and Bactiquant-test rapid bacteria detection technologies. Environmental Technology Verification Report, http://www.epa.gov/nrmrl/std/etv/pubs/600r12002/600r12002vr.pdf (2011).

USCG, Standards for living organisms in ships' ballast water discharged in U.S. waters. Federal Register, 77 (2012) 17254-17320.

USEPA, Web page—Water: Habitat Protection: Invasive Species. http://water.epa.gov/type/oceb/habitat/invasive_species_index.cfm, Accessed Jun. 10, 2012 (2012).

Vanderploeg H A, Liebig J R, Nalepa T F, Fahnenstiel G L, Pothoven S A, *Dreissena* and the disappearance of the spring phytoplankton bloom in Lake Michigan. Journal of Great Lakes Research, 36 (2010) 50-59.

Welschmeyer N, Maurer B, Fluorescein diacetate (FDA): A bulk viability assay for ballast treatment testing. http://www.psmfc.org/ballast/wordpress/wp-content/uploads/2010/01/WelschmeyerPBWG-2010-Recovered.pdf, (accessed Jun. 15, 2012). (2010).

Wright D A, Dawson R, Caceres V, Orano-Dawson C E, Kananen G E, Cutler S J, Cutler H G, Shipboard testing of the efficacy of SeaKleen (R) as a ballast water treatment to eliminate non-indigenous species aboard a working tanker in Pacific waters. Environmental Technology, 30 (2009) 893-910.

While specific embodiments have been described above with reference to the disclosed embodiments and examples, such embodiments are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. An automated device for detecting viable organisms in a fluid, comprising:
  a first chamber adapted to receive a fluid to be tested,
  a second chamber adapted to receive backwash fluid,
  a third chamber adapted to receive discarded fluid,
  a fourth chamber adapted to contain a substrate,
  a vessel adapted to receive filtered fluid for testing, at least one filter assembly containing one or more filters having an influent side and an effluent side,
two or more pumps,
a vessel,
two or more valves,
an injection apparatus, and
a detection apparatus, selected from the group consisting of a fluorimeter, a spectrometer, or a sensor,
wherein the two or more pumps and two or more valves are selectively controlled to form a first, second and third fluid communication path configurations, wherein in the first configuration the fluid to be tested is forced from the first chamber through the at least one filter assembly, wherein contaminants within the fluid to be tested are concentrated on the influent side of the one or more filters and fluid passing through the at least one filter assembly is provided to the third chamber to be discarded, wherein in the second configuration the backwash fluid is forced from the second chamber to the filter assembly, wherein the backwash fluid is provided to the effluent side of the one or more filters and causes the contaminants concentrated on the influent side of the one or more filters to be passed into the vessel, wherein in the third configuration the injection apparatus injects an amount of the substrate from the fourth chamber into the vessel, wherein the detection apparatus detect the contaminants captured within the vessel based on interaction between the contaminants and the injected substrate, wherein the injection apparatus is a substrate injection apparatus, comprising a syringe reservoir, a syringe pump, an electronic rotary valve and a controller.

2. The device of claim 1, wherein the valves control the flow of fluids through the chambers to implement the first, second, and third configurations.

3. The device of claim 1, wherein the device is monitored from a remote location.

4. The device of claim 1, wherein the contaminants detected include the number of viable microorganisms in a fluid.

* * * * *